United States Patent
Stalter et al.

(10) Patent No.: US 11,991,845 B2
(45) Date of Patent: May 21, 2024

(54) METHODS AND SYSTEMS FOR CABLE MANAGEMENT

(71) Applicant: GE Precision Healthcare LLC, Milwaukee, WI (US)

(72) Inventors: Ross Christopher Stalter, Hartland, WI (US); Brian Kufahl, Colgate, WI (US); Paul Vermey, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 1247 days.

(21) Appl. No.: 16/660,731

(22) Filed: Oct. 22, 2019

(65) Prior Publication Data

US 2021/0120690 A1   Apr. 22, 2021

(51) Int. Cl.
*H05K 5/02* (2006.01)
*A61B 8/00* (2006.01)
*A61B 8/12* (2006.01)
*H05K 5/00* (2006.01)

(52) U.S. Cl.
CPC ............ *H05K 5/0247* (2013.01); *A61B 8/12* (2013.01); *A61B 8/461* (2013.01); *H05K 5/0086* (2013.01)

(58) Field of Classification Search
CPC ...... H05K 5/0086; H05K 5/0247; A61B 8/12; A61B 8/4427; A61B 8/461; A61B 8/56
See application file for complete search history.

(56) References Cited

U.S. PATENT DOCUMENTS

| 2007/0049073 A1* | 3/2007 | Hill | H01R 4/646 439/98 |
| 2018/0084664 A1* | 3/2018 | Giroux | H05K 7/1491 |
| 2020/0359112 A1* | 11/2020 | Lund | H04Q 1/09 |

FOREIGN PATENT DOCUMENTS

| CN | 105620293 A | 6/2016 |
| CN | 104797871 B | 11/2017 |
| WO | 2019118326 A1 | 6/2019 |

OTHER PUBLICATIONS

CN application 202011081603.0 filed Oct. 10, 2020—Office Action dated Nov. 2, 2021; 9 pages.
CN104797871 English Abstract, Espacenet search results Feb. 1, 2022; 1 page.
CN patent application 202011081603.0 filed Oct. 10, 2020—2nd Office Action dated Jul. 8, 2022; 10 pages.

\* cited by examiner

*Primary Examiner* — Terrell S Johnson

(57) ABSTRACT

Various methods and systems are provided for cable management for portable electronic medical devices. In one embodiment, a system comprises: a frame for a portable electronic medical device, the frame including a first wall and an opposing, second wall forming inner surfaces of a channel; and a cable coupler adapted to seat within the channel, including: counterpart outer surfaces shaped to engage the inner surfaces; and a passage shaped to enclose a portion of a cable.

12 Claims, 13 Drawing Sheets

METHODS AND SYSTEMS FOR CABLE MANAGEMENT

FIELD

Embodiments of the subject matter disclosed herein relate to cable management for portable electronic medical devices.

BACKGROUND

Portable electronic medical devices, such as portable patient monitors, are often used by clinicians for patient imaging, patient monitoring, determining patient diagnoses, etc. A portable electronic medical device may include multiple ports configured to electronically couple the portable electronic medical device to other electronic devices or accessories, such as ultrasound probes, user input devices such as a mouse and keyboard, a printer, etc. The electronic devices or accessories may be in electronic communication with the portable electronic medical device via respective cables coupled to the ports of the portable electronic medical device.

BRIEF DESCRIPTION

In one embodiment, a system comprises: a frame for a portable electronic medical device, the frame including a first wall and an opposing, second wall forming inner surfaces of a channel; and a cable coupler adapted to seat within the channel, including: counterpart outer surfaces shaped to engage the inner surfaces; and a passage shaped to enclose a portion of a cable.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
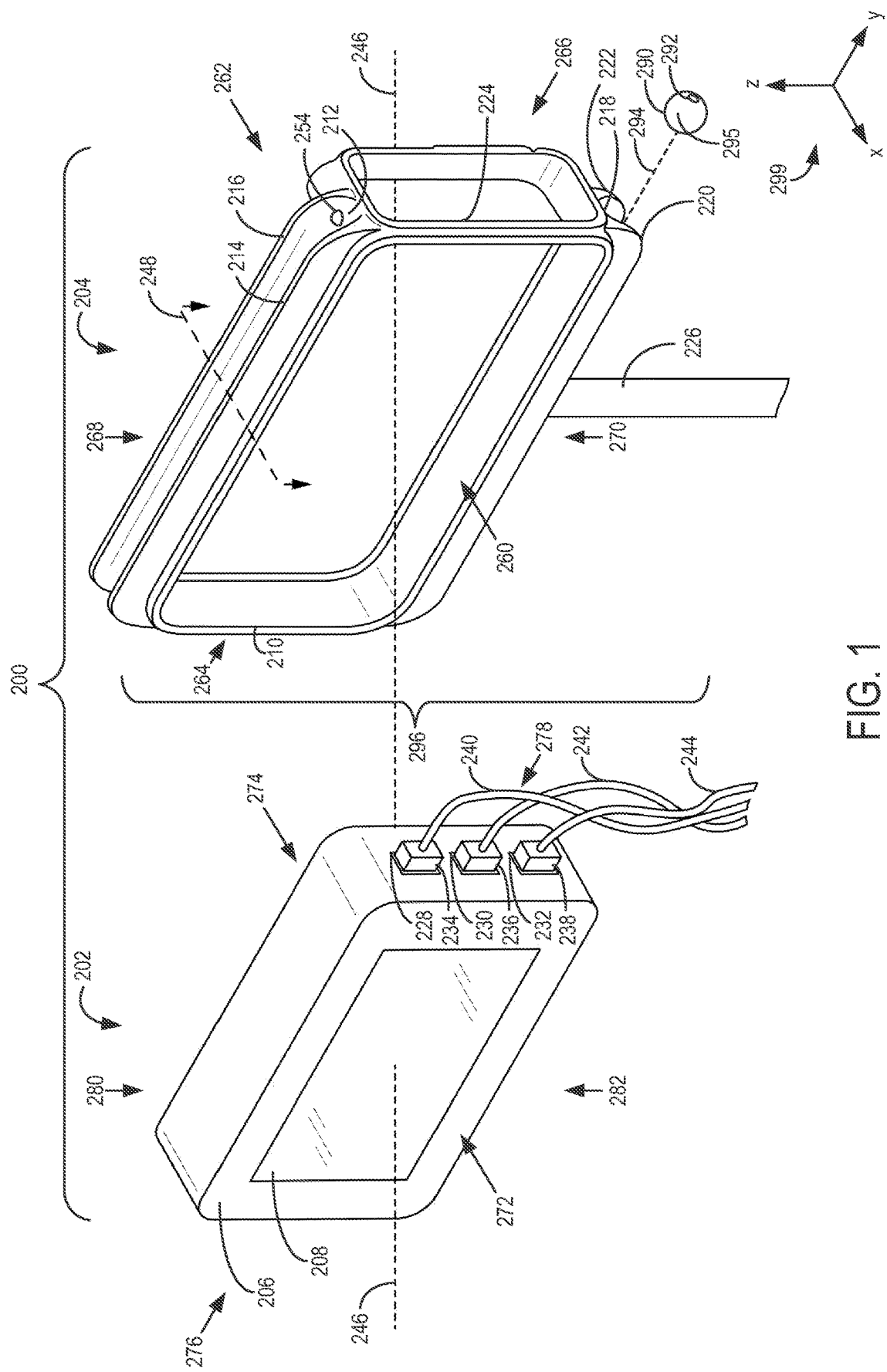
FIG. 1 shows an exploded view of a portable electronic medical device including a cable management system.
Figure 2:
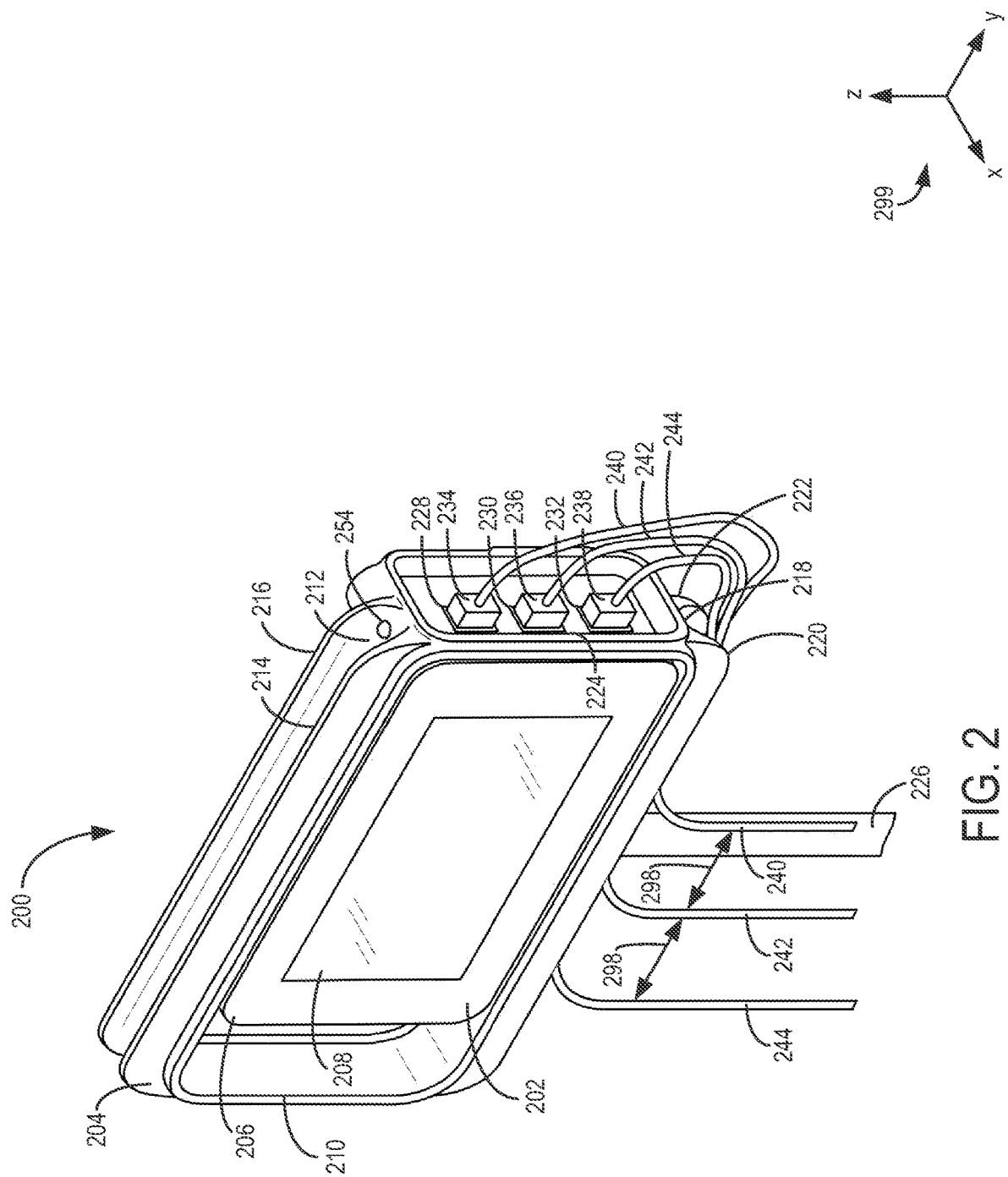
FIG. 2 shows an assembled view of the portable electronic medical device with cable management system of FIG. 1.
Figure 3:
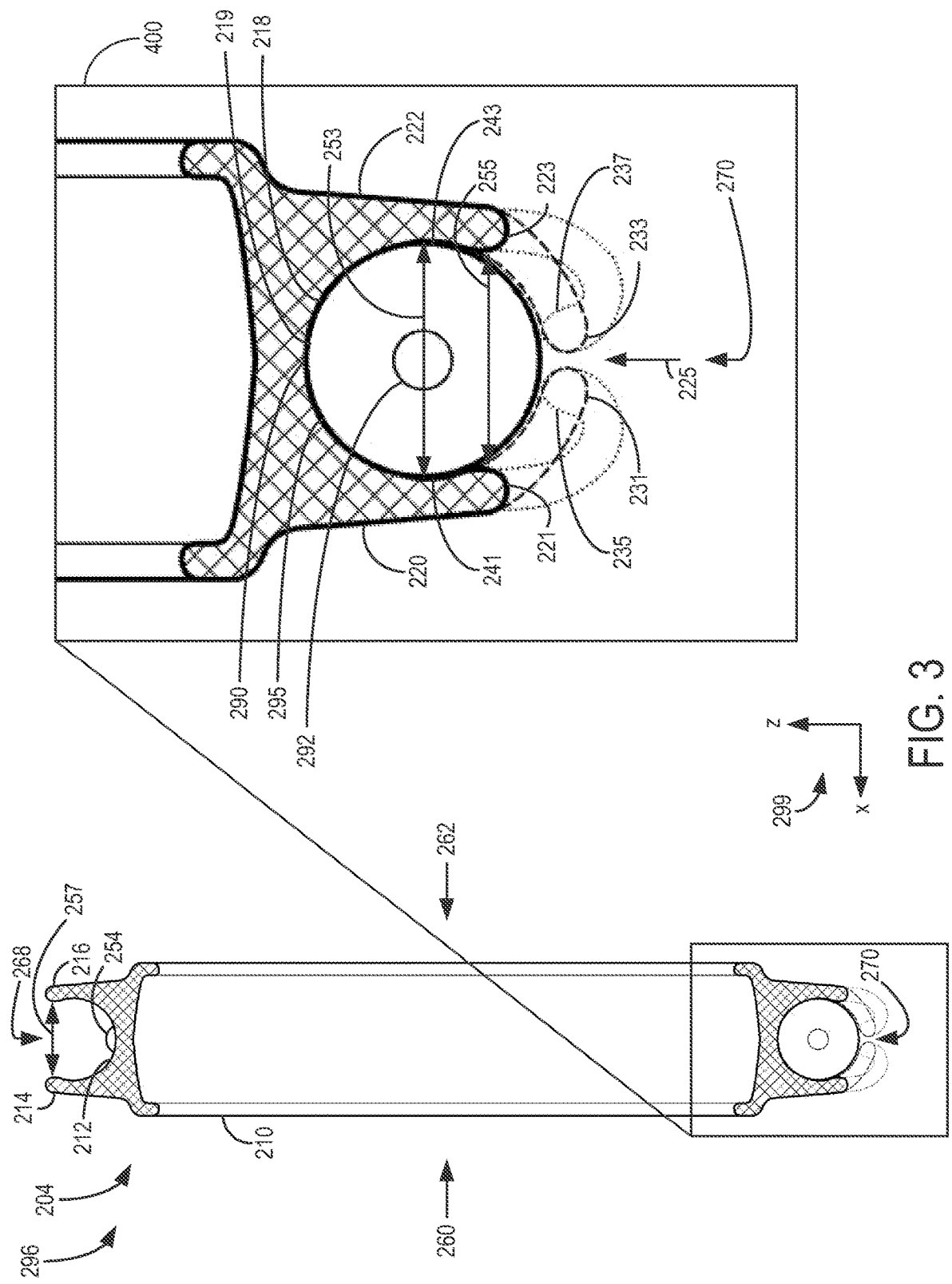
FIG. 3 shows a sectional view of a frame of the cable management system of the portable electronic medical device of FIGS. 1-2.
Figure 11:
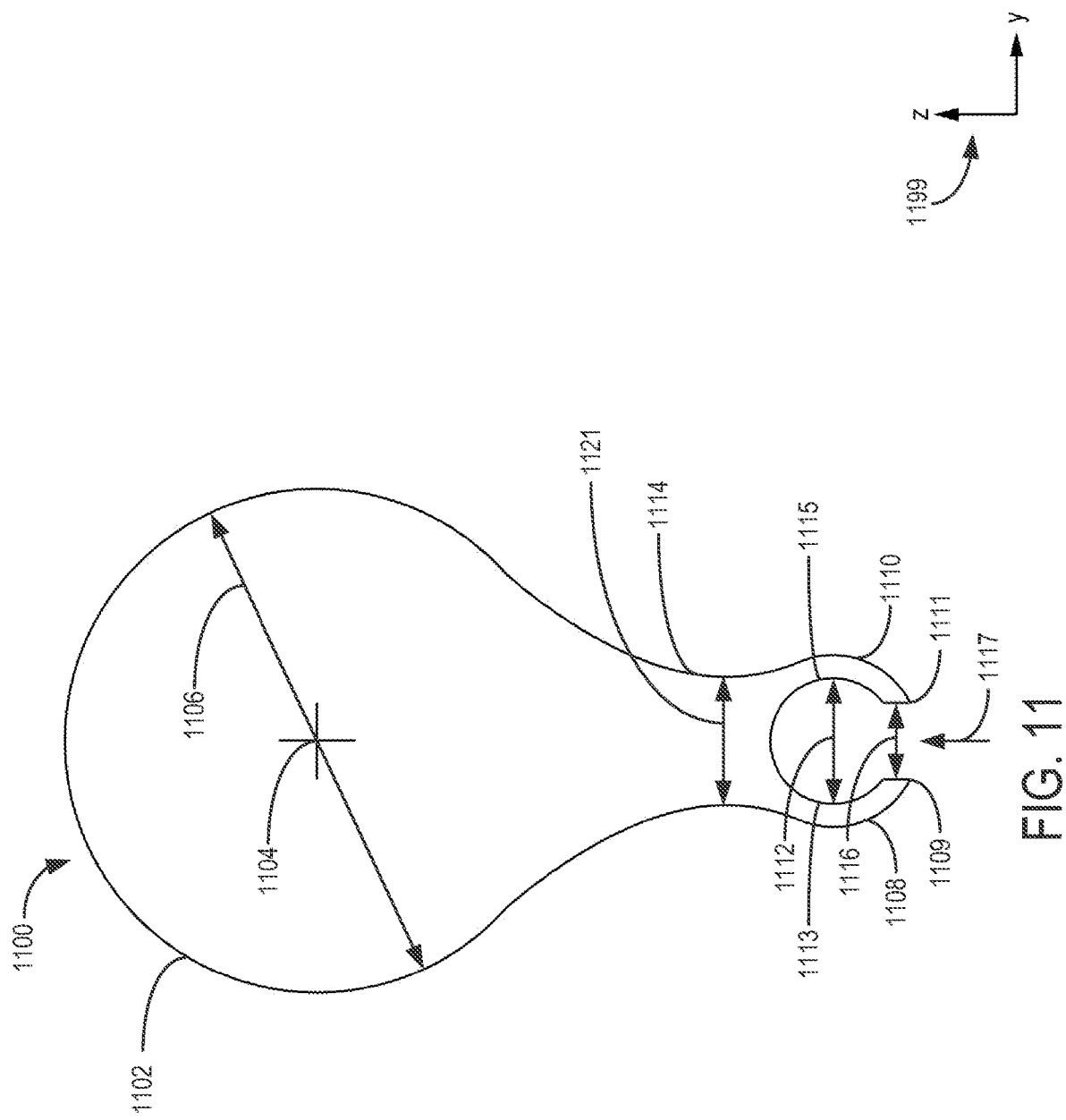
FIG. 11 shows a side view of another cable coupler for a cable management system.
Figure 12:
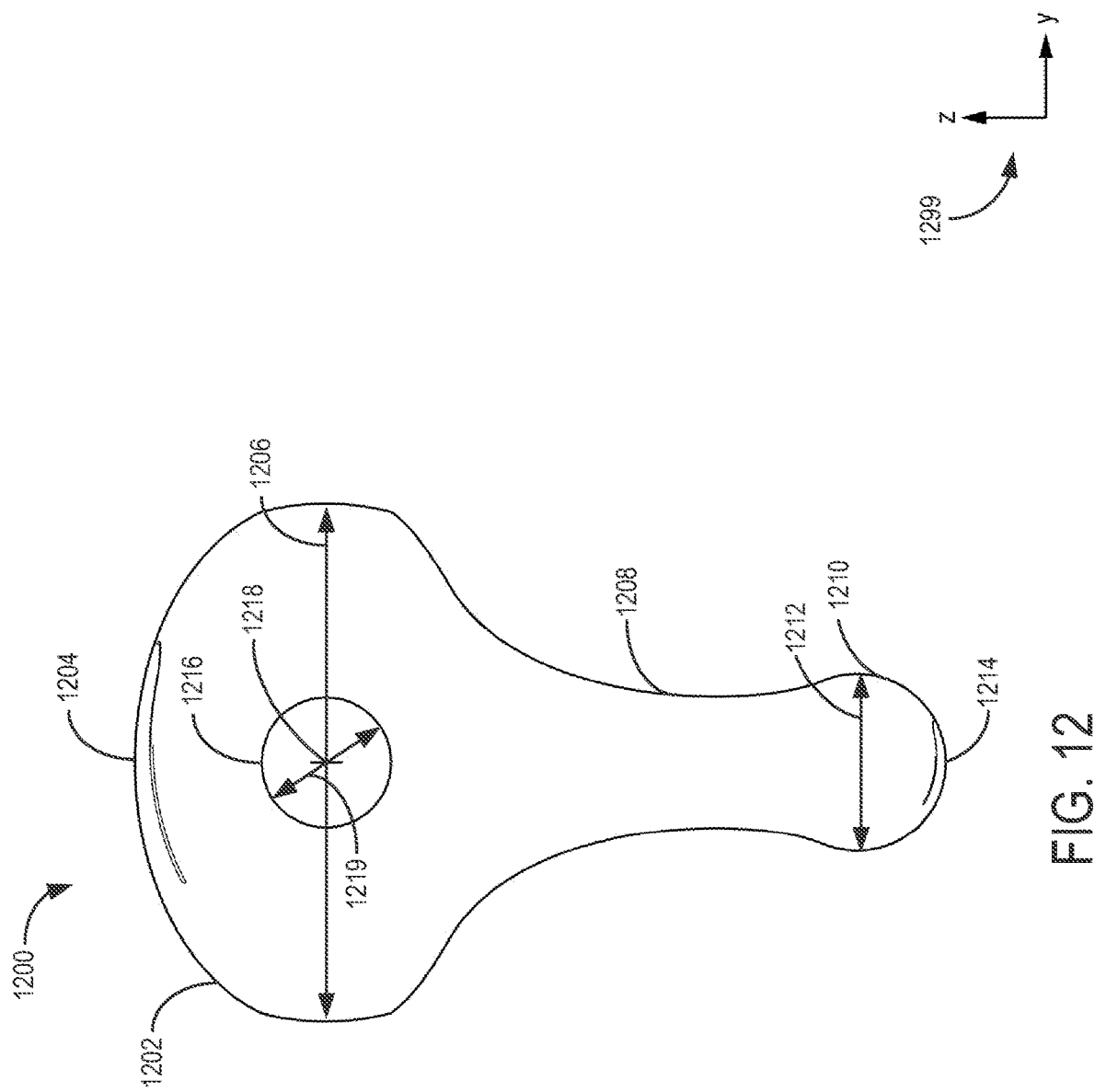
FIG. 12 shows a side view of another cable coupler for a cable management system.
Figure 13:
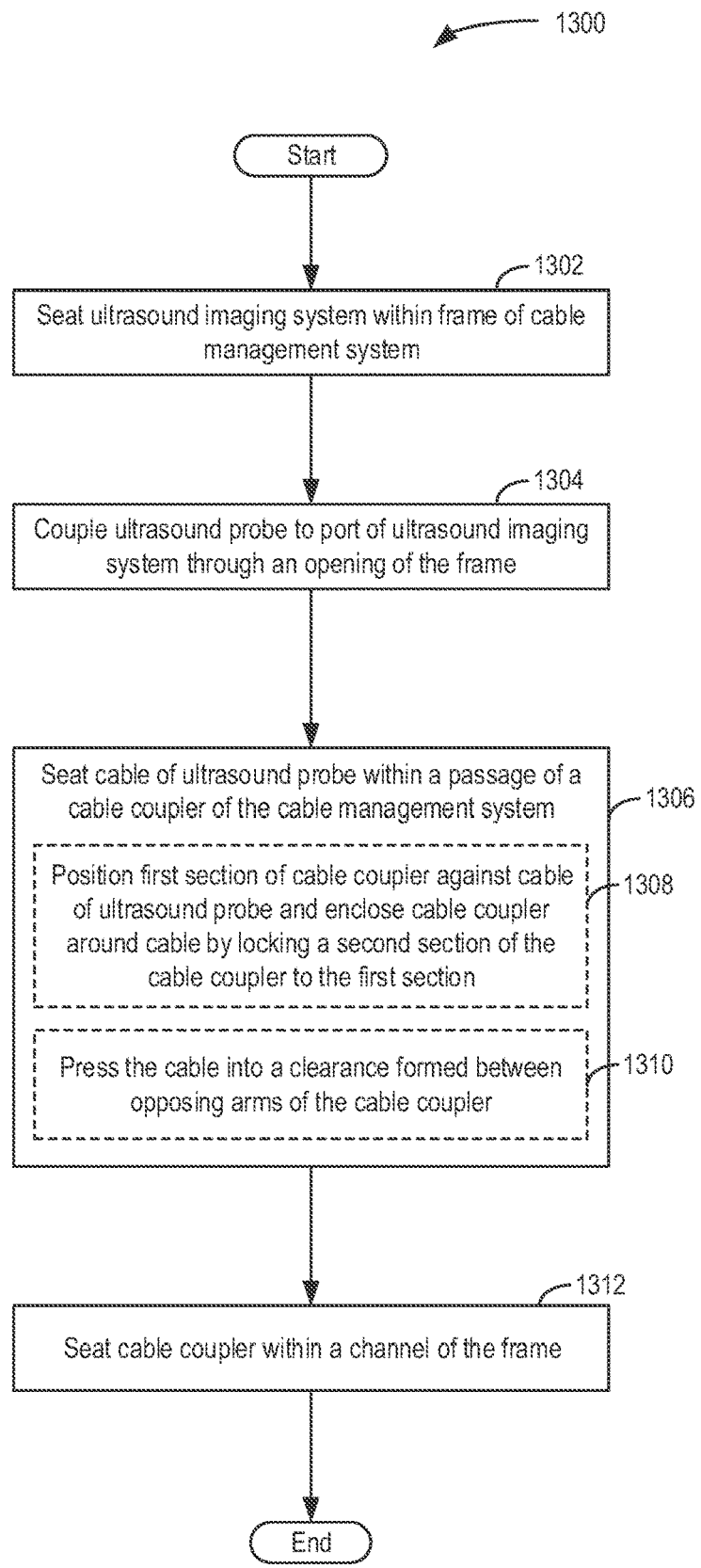
FIG. 13 shows a flowchart illustrating a method for cable management via a cable management system.

The following description relates to various systems and methods for cable management for portable electronic medical devices. A portable electronic medical device, such as the portable electronic medical device shown schematically by FIG. 4, may include one or more electronic accessories, such as user input devices. The accessories may be electronically coupled to the portable electronic medical device via respective cables, as shown by FIG. 1. A position of the cables may be maintained by a cable management system, as shown by FIG. 2. The cable management system includes a frame having an opening shaped to receive the portable electronic medical device, and the frame is formed with one or more channels. The cable management system further includes at least one cable coupler, as shown by FIGS. 5-9, shaped to seat within the one or more channels, as shown by FIG. 3. Each cable coupler includes a passaged shaped to receive a respective cable of one of the accessories. In some embodiments, the passage may extend through a thickness of the cable coupler, as shown by FIGS. 5-10. In other embodiments, the passage may be formed between opposing arms of the cable coupler, as shown by FIG. 11. Further, in some embodiments, the cable coupler may seat within the one or more channels via engagement of a spherical portion of the cable coupler with corresponding walls of the channels, and in other embodiments, as shown by FIG. 12, the cable coupler may include a rounded but non-spherical portion configured to engage with the walls. By seating the portable electronic medical device in the frame, coupling the cables of the accessories to respective cable couplers, and seating the cable couplers within a channel of the frame (as illustrated by the flowchart of FIG. 13), the frame maintains a position of the cables relative to the portable electronic medical device. In this way, a likelihood of tangling and/or knotting of the cables may be reduced, and the different cables may be more easily visually distinguished by a user of the portable electronic medical device.

Referring now to FIG. 1, an assembly 200 including a cable management system 296 is shown. FIG. 1 shows the assembly 200 in an unassembled configuration, FIG. 2 shows the assembly 200 in an assembled configuration, and FIG. 3 shows a sectional view of a frame 204 of the cable management system 296 with the assembly 200 in the unassembled configuration. Reference axes 299 are included by FIGS. 1-3 for comparison of the views shown.

The frame 204 of the cable management system 296 is configured to support at least one cable coupler 290. In the embodiment shown, the cable coupler 290 has a spherical shape and is sized to fit within a channel, such as channel 218, of the frame 204, as described further below. However, in other embodiments (such as the embodiments described below with reference to FIGS. 11-12), the cable coupler 290 may have a different shape (e.g., a tapered shape, rectangular shape, hexagonal shape, or other non-spherical shape).

The assembly 200 includes a portable electronic medical device 202. In some embodiments, portable electronic medical device 202 may be the portable electronic medical device 100 described below with reference to FIG. 4. For example, portable electronic medical device 202 may include an electronic controller including a processor and memory housed within housing 206, with the electronic controller, processor, and memory being similar to the electronic controller 123, processor 116, and memory 120, respectively, described below with reference to FIG. 4. Portable electronic medical device 202 further includes a display device 208 (e.g., display screen), with the display device 208 coupled directly with the housing 206 and facing outward from an interior of the housing 206. In some embodiments, display device 208 may be similar to the display device 118 described below with reference to FIG. 4. For example, the display device 208 may be a touch screen and may be configured to display a GUI. An operator of the portable electronic medical device 202 may interact with the GUI (e.g., touch the touch screen) in order to select commands associated with each specific user interface icon in order to initiate various functions controlled by the GUI (e.g., for adjusting patient monitoring parameters of the portable electronic medical device 202).

The portable electronic medical device 202 may include one or more accessories electronically coupled to the electronic controller of the portable electronic medical device 202 (e.g., the processor, memory, and other components housed within the housing 206). Each of the accessories may be coupled to the electronic controller via a respective port formed in the housing 206.

In the embodiment shown by FIG. 1, the portable electronic medical device 202 includes a first port 228, a second port 230, and a third port 232, with the first, second, and third ports arranged at a second side 278 of the housing 206 opposite to a first side 276, and with the display device 208 positioned at a first end 272 of the housing 206 and extending in a direction from the first side 276 to the second side 278 (e.g., the direction of the y-axis of reference axes 299). First port 228, second port 230, and third port 232 may be referred to herein as electronic communication ports. In this configuration, the first port 228, second port 230, and third port 232 are not arranged at a second end 274 opposite to the first end 272, but instead are arranged at the second side 278 extending between the first end 272 and second end 274. Although the first port 228, second port 230, and third port 232 are described herein, the portable electronic medical device 202 may include additional ports configured to be in electronic communication with the electronic controller of portable electronic medical device 202. For example, the portable electronic medical device 202 may include additional ports arranged at the first side 276, second end 274, etc., and a position of cables coupled to the additional ports may be managed via the cable management system 296 in a similar way compared to cables coupled to the first port 228, second port 230, and third port 232. However, for discussion purposes, only the first port 228, second port 230, and third port 232 are described herein.

As shown by FIG. 1, a first connector 234 is coupled to the first port 228, a second connector 236 is coupled to the second port 230, and a third connector 238 is coupled to the third port 232. A first end of each of the connectors (e.g., first connector 234, second connector 236, and third connector 238) is electronically coupled to the respective port of the portable electronic medical device 202, and a second end of each of the connectors is electronically coupled to a respective cable. Each cable may be electronically coupled to a corresponding accessory (e.g., mouse, keyboard, medical imaging device, etc.). For example, first connector 234 is electronically coupled with first cable 240, and first cable 240 may additionally be electronically coupled with a first accessory. Similarly, second connector 236 is electronically coupled with second cable 242, with second cable 242 additionally electronically coupled with a second accessory, and third connector 238 is electronically coupled with third cable 244, with third cable 244 additionally electronically coupled to a third accessory (e.g., a keyboard, mouse, etc.).

In the unassembled configuration, a position of each of the first cable 240, second cable 242, and third cable 244 is not maintained by the cable management system 296. For example, as shown by FIG. 1, the housing 206 of the portable electronic medical device 202 is not seated within the frame 204 of the cable management system 296. As a result, the first cable 240, second cable 242, and third cable 244 are each free to move independently relative to the housing 206 (e.g., bend, twist, etc. relative to the housing 206 and relative to each other). During some conditions, such as conditions in which the portable electronic medical device 202 is moved from one location to another (e.g., moved from a first room of a facility, such as a hospital, to a second room of the facility), movement of the first cable 240, second cable 242, and third cable 244 relative to the housing 206 and/or relative to each other may result in undesirable tangling and/or knotting of the cables. Additionally, movement of the portable electronic medical device 202 with the cables in this configuration (e.g., the configuration in which the cables are free to move relative to the housing 206 and each other) may increase a likelihood of undesirable catching of one or more of the cables on surrounding fixtures (e.g., equipment within the facility, such as tables, beds, etc.).

By utilizing the cable management system 296 in combination with the portable electronic medical device 202, the cable management system 296 may maintain the position of the first cable 240, second cable 242, and third cable 244 relative to the housing 206 in order to reduce the likelihood of cable tangling, catching, etc. Further, as described below, the cable management system 296 may visually distinguish each cable from each other cable via different colors and/or shapes of cable couplers in order to increase organization of the cables and reduce a cognitive load of an operator of the portable electronic medical device 202 (e.g., a clinician).

The cable management system 296 includes frame 204 having a main opening 210 configured to receive the housing 206 of the portable electronic medical device 202. In some embodiments, frame 204 may be formed from a semi-rigid material (e.g., plastic) and/or may include one or more flexible layers (e.g., rubber) in order to expand during conditions in which the housing 206 of the portable electronic medical device 202 is inserted through the main opening 210. After the housing 206 has been fully inserted into the main opening 210 (e.g., the housing 206 is seated within the frame 204), the frame 204 may contract in order to maintain the seated position of the housing 206 within the frame 204. As shown by FIG. 1, the main opening 210 of the frame 204 is positioned at a first end 260 of the frame, opposite to a second end 262. Second end 262 may include an opening similar to the main opening 210, such that the housing 206 of the portable electronic medical device 202 may be seated within the frame 204 by inserting the housing 206 through the corresponding opening at either of the first end 260 or second end 262 (e.g., in a direction of assembly axis 246). In the embodiment shown, the frame 204 includes a side opening 224 positioned at a second side 266 of the frame 204, opposite to first side 264.

During conditions in which the portable electronic medical device 202 is seated within the frame 204, the second side 278 of the housing 206 may be arranged at the second side 266 of the frame 204. In this configuration, each of the first port 228, second port 230, and third port 232 of the housing 206 may be accessible via the side opening 224 of the frame 204, as illustrated by FIG. 2 and described further below. Further, with the housing 206 seated within the frame 204, the display device 208 may be accessible (e.g., viewable and available for interaction by the operator) through the main opening 210 of the frame 204. In the embodiment shown, the frame 204 is coupled to a support stand 226, which may include one or more feet, casters, etc. configured to maintain the frame 204 in an upright position (e.g., an elevated position relative to a ground surface on which the support stand 226 sits). However, frame 204 may be removably coupled to the support stand 226 such that the frame 204 may be decoupled and utilized separately from the support stand 226. For example, during conditions in which housing 206 is seated within the frame 204 and the frame 204 is not coupled to the support stand 226, the frame 204 may be utilized to maintain a position of the cables coupled to the portable electronic medical device 202 (e.g., first cable 240, second cable 242, and third cable 244) as the portable electronic medical device 202 is moved one location to another, or utilized by the operator in a handheld configuration (e.g., a configuration in which the display device 208 is a touch screen and is interacted with in order view data such as patient information, monitor patient parameters via one or more accessories coupled to the portable electronic medical device 202, etc. while the portable electronic medical device 202 is supported by the operator and/or not mounted to support stand 226).

In the embodiment shown by FIG. 1, the frame 204 includes channels positioned at top end 268 and bottom end 270, with the bottom end 270 being positioned closer than the top end 268 to the ground surface on which support stand 226 sits during conditions in which the frame 204 is coupled to the support stand 226. Bottom end 270 is arranged perpendicular to the main opening 210 and side opening 224 (e.g., bottom end 270 is arranged perpendicular to first end 260 and second side 266, with the main opening 210 positioned at first end 260 and with the side opening 224 positioned at second side 266). Specifically, channel 212 is positioned at top end 268 and is formed between a first wall 214 and second wall 216, while channel 218 is positioned at bottom end 270 and is formed between a third wall 220 and fourth wall 222. The channel 212 and the channel 218 are each shaped to receive cable coupler 290, with the cable coupler 290 having a counterpart shape relative to the shape of the channel 212 and channel 218, as described further below. In some embodiments, the channels (e.g., one or both of the channel 212 and channel 218) may include one or more protrusions (e.g., protrusion 254) configured to maintain a position of the cable coupler 290. For example, protrusion 254 is shown arranged within the channel 212 and positioned closer to the second side 266 of the frame 204 than the first side 264. During conditions in which the cable coupler 290 is seated within the channel 212, the protrusion 254 may reduce a likelihood of the cable coupler 290 becoming unseated from the channel 212 (e.g., due to a sliding motion of the cable coupler 290 within the channel 212 in a direction toward the second side 266). Although only the protrusion 254 is shown, in some embodiments, the channel 212 may include a similar protrusion positioned closer to the first side 264 than the second side 266. Similarly, channel 218 may include one or more similar protrusions positioned toward the first side 264 and/or second side 266.

Seating the cable coupler 290 within one of the channel 212 or channel 218 may include pressing the cable coupler 290 against the corresponding walls of the respective channel in order to momentarily expand a length between the walls, as described further below. While the cable coupler 290 is seated within one of the channels, a position of the cable coupler 290 within the respective channel may be adjusted by the operator by sliding the cable coupler 290 within the respective channel. For example, as shown by FIG. 1, the operator may slide cable coupler 290 in a direction of axis 294 during conditions in which the cable coupler 290 is seated within the channel 218. The cable coupler 290 includes a passage 292 shaped to enclose a portion of a corresponding cable, such as one of first cable 240, second cable 242, or third cable 244, in order to maintain a position of the corresponding cable relative to the cable coupler 290. By seating the cable coupler 290 within the channel 218, the position of the cable coupler 290 is maintained by the frame 204 while the cable coupler 290 maintains the position of the corresponding cable. As a result, the position of the corresponding cable is maintained relative to the frame 204.

Referring now to FIG. 2, the assembly 200 is shown in the assembled configuration. Specifically, FIG. 2 shows the portable electronic medical device 202 seated within the frame 204. As described above, each of first port 228, second port 230, and third port 232 are accessible via the side opening 224 of the frame 204. In the configuration shown by FIG. 2, the positions of the first cable 240, second cable 242, and third cable 244 are each maintained via the cable management system 296. Specifically, in the unassembled configuration shown by FIG. 1, the first cable 240, second cable 242, and third cable 244 are free to move relative to the portable electronic medical device 202, as described above. However, in the assembled configuration shown by FIG. 2, each cable is fixed in position at the channel 218 at the bottom of the frame 204 by a respective cable coupler (e.g., cable coupler 290 shown by FIG. 2). For example, first cable 240 may be coupled with cable coupler 290 shown by FIG. 2, second cable 242 may be coupled with a second cable coupler similar to the cable coupler 290, and third cable 244 may be coupled with a third cable coupler similar to the cable coupler 290.

Each of the cable couplers is seated within the channel 218, with the position of each cable coupler maintained by the third wall 220 and fourth wall 222 of the channel 218. Because each cable coupler is seated within the channel 218 and maintained in position relative to the frame 204 by the third wall 220 and fourth wall 222 of the channel 218, and because each of first cable 240, second cable 242, and third cable 244 is coupled to a respective cable coupler seated within channel 218, the position of each of the first cable 240, second cable 242, and third cable 244 is maintained relative to frame 204. As a result, a likelihood of tangling and/or knotting of the cables may be reduced. For example, a clearance 298 between each of the first cable 240, second cable 242, and third cable 244 at the bottom end 270 of the frame 204 may be increased by adjusting the relative spacing of the cable couplers within the channel 218. Increasing the clearance 298 may increase an ease with which an operator of the portable electronic medical device 202 may visually identify each cable, which may decrease a cognitive load of the operator. Further, by maintaining the position of each cable via respective cable couplers at the bottom end 270 of the frame 204, each cable may hang away from the frame 204 in a direction of gravity (e.g., the direction of the z-axis of reference axes 299) and each cable may not overlap with each adjacent cable, which may further increase the ease of identification of each cable and reduce a likelihood of tangling.

In some embodiments, the cable management system 296 may additionally manage one or more cables and/or hoses not electronically coupled to the portable electronic medical device 202. For example, an electronic accessory may be electronically coupled to the portable electronic medical device via first cable 240, and the electronic accessory may be additionally coupled to one or more tubes or hoses (e.g., intravenous tubes). The cable management system 296 may maintain a position of the one or more tubes or hoses in a similar way relative to the management of first cable 240 via cable coupler 290 (e.g., a second cable coupler may be coupled to a first hose and seated within the channel 218 in order to maintain the position of the first hose relative to the frame 204). In some embodiments, the cable management system 296 may maintain a position of one or more tubes, hoses, cables, etc. in a similar way, where the one or more tubes, hoses, cables, etc. are coupled to a device not seated within the frame 204. For example, portable electronic medical device 202 may be seated within the frame 204, with cables coupled to the portable electronic medical device 202 maintained via respective cable couplers seated within the channel 218. An intravenous delivery system, separate from the portable electronic medical device 202 and in proximity to the frame 204, may include one or more tubes, hoses, etc. that are also maintained in position relative to the frame 204 by respective cable couplers seated within one of channel 218 or channel 212.

Referring now to FIG. 3, a cross-sectional view of the frame 204 is shown with the portable electronic medical device 202 removed (e.g., unseated) from the frame 204. FIG. 3 includes inset 400 showing an enlarged view of the channel 218, with cable coupler 290 seated within the channel 218.

As shown by inset 400, the third wall 220 includes terminating end 221, and the fourth wall 222 includes terminating end 223, with a clearance 255 separating the terminating end 221 from the terminating end 223. A length of the clearance 255 is smaller than a diameter 253 of the cable coupler 290. While coupling the cable coupler 290 to the frame 204 (e.g., seating the cable coupler 290 within the channel 218), the cable coupler 290 may be pressed against each of the third wall 220 and fourth wall 222 in direction 225 (e.g., toward the channel 218 from the bottom end 270 of the frame 204) in order to temporarily move the terminating end 221 and terminating end 223 away from each other (e.g., deflect the terminating ends in an outward direction relative to each other) and increase the length of the clearance 255. For example, the third wall 220 and fourth wall 222 may be formed from a rigid material (e.g., plastic) that is able to temporarily bend and/or flex outward during conditions in which force is applied to the third wall 220 and fourth wall 222 (as described below). During conditions in which the third wall 220 and fourth wall 222 are flexed outward relative to each other, the rigidity of the material results in a restoring force applied to each of the third wall 220 and fourth wall 222 in an inward direction (e.g., toward each other).

In some embodiments, the walls (e.g., third wall 220 and fourth wall 222) may have a greater length than the length shown by FIG. 3. For example, third wall 220 may extend further such that the terminating end 221 is in alternate position 231, and the fourth wall 222 may extend further such that the terminating end 223 is in alternate position 233, with alternate position 231 and alternate position 233 indicated by dashed lines. In other embodiments, the third wall 220 and fourth wall 222 may have a greater curvature such that the arms are shaped as hooks (as indicated by alternate arm position 235 and alternate arm position 237, each shown in dotted lines). Increasing the curvature of the arms may increase an ability of the arms to maintain the cable coupler 290 within the channel 218. Although the third wall 220 and fourth wall 222 are described above with regard to alternate positions 231, 233, 235, and 237, it should be noted that the first wall 214 and second wall 216 of the channel 212 may include a similar configuration (e.g., first wall 214 and second wall 216 may be shaped as hooks and/or have increased length relative to the embodiment shown by FIG. 3).

During conditions in which the cable coupler 290 is pressed into the channel 218 in the direction 225, the pressing force against the third wall 220 and fourth wall 222 by the cable coupler 290 causes the terminating ends to move away from each other until the length of the clearance 255 is at least a same amount of length as the diameter 253 of the cable coupler 290. The cable coupler 290 may then fit through the clearance 255 and seat against an inner surface 219 of the channel 218 as well as inner surface 241 of third wall 220 and inner surface 243 of fourth wall 222. After seating the cable coupler 290 within the channel 218 (e.g., positioning outer surfaces 295 of the cable coupler 290 in face-sharing contact with the inner surface 219, inner surface 241, and inner surface 243), the restoring force acting on the third wall 220 and fourth wall 222 reduces the length of the clearance 255 to less than the diameter 253 and maintains the cable coupler 290 in the seated position within the channel 218. Further, in some embodiments, one or more outer surfaces of the cable coupler 290 may be formed from a material (e.g., rubber) configured to increase an amount of friction between the cable coupler 290 and the inner surface 219, inner surface 241 of third wall 220, and inner surface 243 of fourth wall 222 forming the channel 218. In other embodiments, one or more of the inner surface 219, inner surface 241 of third wall 220, and inner surface 243 of fourth wall 222 may be formed of the material configured to increase the amount of friction against the cable coupler 290. In such embodiments, the increased friction resulting from the material may further maintain the position of the cable coupler 290 within the channel 218, in addition to the force applied to the cable coupler 290 by the third wall 220 and fourth wall 222 as the restoring force drives the third wall 220 and fourth wall 222 toward each other.

In the first configuration in which the cable coupler 290 is not seated within the channel 218, the third wall 220 and fourth wall 222 are separated by a smaller amount of length relative to the configuration in which the cable coupler 290 is seated within the channel 218. As described above, cable coupler 290 may be seated within either of channel 212 or channel 218. In the embodiment shown by FIG. 3, the cable coupler 290 is seated within channel 218, while channel 212 does not include a cable coupler seated therein. The channel 212 and channel 218 each have a same shape in the embodiment shown by FIG. 3, such that during conditions in which neither of the channel 212 or channel 218 include a cable coupler seated therein, the first wall 214 and second wall 216 are spaced apart from each other by a same amount as an amount of space between the third wall 220 and fourth wall 222. Further, a relative size and curvature of the first wall 214 and second wall 216 in the embodiment shown by FIG. 3 is the same as a relative size and curvature of the third wall 220 and fourth wall 222.

Due to the channel 212 being in the first configuration in which the cable coupler 290 is not seated within the channel 212, the first wall 214 and second wall 216 are not deformed (e.g., bent, expanded, etc.) by the cable coupler 290. As a result, the first wall 214 and second wall 216 are separated by clearance 257. However, the channel 218 is in the second configuration in which the cable coupler 290 is seated within the channel 218, and the third wall 220 and fourth wall 222 are deformed (e.g., pushed outward from each other) by the cable coupler 290. As a result, the third wall 220 and fourth wall 222 are separated by clearance 255. In the embodiment shown by FIG. 3, the clearance 255 has a greater amount of length than the clearance 257 due to the deformation of the third wall 220 and fourth wall 222 resulting from the seating of the cable coupler 290 within the channel 218. However, in some embodiments, the length of clearance 255 may be the same both of the first configuration and second configuration (e.g., the length may be the same during conditions in which the cable coupler 290 is not seated within the channel 218 relative to conditions in which the cable coupler 290 is seated within the channel 218).

It should be noted that although the length of the clearance 255 may be the same in some embodiments during conditions in which no portion of the cable coupler 290 is seated within the channel 218 and during conditions in which the cable coupler 290 is fully seated within the channel 218, the length of the clearance 255 is increased during the seating of the cable coupler 290 within the channel 218. For example, transitioning from the first configuration in which no portion of the cable coupler 290 is seated within the channel 218 to the configuration in which the cable coupler 218 is fully seated within the channel 218 includes momentarily expanding the length of the clearance 255 by moving the third wall 220 and fourth wall 222 apart from each other (e.g., by pressing the cable coupler 290 into the channel 218 between the third wall 220 and fourth wall 222). Then, once the cable coupler 290 is fully seated within the channel 290, the third wall 220 and fourth wall 222 may contract toward each other (e.g., bend toward their respective initial positions) and reduce the length of the clearance 255 to maintain the cable coupler 290 within the channel 218.

In the embodiment shown by FIG. 3, the cable coupler 290 has a relatively round, spherical shape. The third arm 220 and fourth arm 222 each have a counterpart shape relative to the shape of the cable coupler 290, such that the cable coupler 290 seats against the surfaces of third arm 220 and fourth arm 222 in the channel 218 with little or no clearance between the outer surfaces of the cable coupler 290 and the counterpart surfaces of the third arm 220 and fourth arm 222 (e.g., surfaces of the third arm 220 and fourth arm 222 configured to be positioned in face-sharing contact with the cable coupler 290). For example, a radius of curvature of each of the inner surface 219, inner surface 241 of third arm 220, and inner surface 243 of fourth arm 222 may be the same as a radius of curvature of the outer surfaces 295 of cable coupler 290.

Although the cable coupler 290 is described above as an example, the cable management system 296 may include multiple cable couplers similar to (or the same as) the cable coupler 290. Further, cable management system 296 may include one or more cable couplers similar to the cable couplers described below with reference to FIGS. 5-12. In some embodiments, one or more of the cable couplers may be color coded such that the user may more easily visually identify each cable coupler. For example, a first cable coupler of the cable management system 296 may have a first color (e.g., red), and a second cable coupler of the cable management system 296 may have a second color (e.g., green), with the first cable coupler coupled to a first cable (e.g., first cable 240), and with the second cable coupler coupled to a second cable (e.g., second cable 242). During conditions in which the user desires to adjust a position of the first cable by adjusting the position of the respective cable coupler within the channel of the frame of the cable management system, the user may more easily identify the first cable coupler coupled to the first cable due to the first cable coupler having the first color. Similarly, during conditions in which the user desires to adjust a position of the second cable by adjusting the position of the respective cable coupler within the channel of the frame of the cable management system, the user may more easily identify the second cable coupler coupled to the second cable due to the second cable coupler having the second color. Configuring the cable couplers to have different colors may result in increased ease of use and reduced cognitive load on the user.

In some embodiments, one or more of the cables may have a different color relative to each other cable coupled to the portable electronic medical device 202. For example, the first cable 240 may be a first color (e.g., blue), and the second cable 242 may be a second color (e.g., orange). A first cable coupler coupled to the first cable may have the same color as the first cable 240 (e.g., blue), and a second cable coupler coupled to the second cable may have the same color as the second cable (e.g., orange). This configuration may further result in increased ease of use and reduced cognitive load on the user due to easier identification of the cable coupler associated (e.g., coupled) with each cable.

Although the channel 212 and channel 218 are described above as being positioned at the top end 268 and bottom end 270, respectively, of the frame 204, in other embodiments the channel 212 and channel 218 may be positioned at different portions of the frame 204. For example, channel 218 may be positioned at second side 266, and/or channel 212 may be positioned at first side 264. As another example, channel 218 may be positioned at bottom end 270 and channel 212 may be positioned at second side 266. As yet another example, channel 212 may be positioned at first end 260 and channel 218 may be positioned at second end 262. Other embodiments are contemplated. Further, in some embodiments, one or each of channel 212 and channel 218 may have a different length. For example, channel 218 may span only a portion of the surface of the frame 204 at bottom end 270 (e.g., channel 218 may have a length approximately half of the length along bottom end 270 shown by FIG. 1). Further, in some embodiments, the frame 204 may include additional channels similar to channels 212 and 218, such as one or more additional channels positioned at the first side 264, second side 266, etc., with each channel shaped to receive the cable coupler 290 such that the cable coupler 290 may be seated at a plurality of different sides or ends of the frame 204 via the channels.

Figure 4:
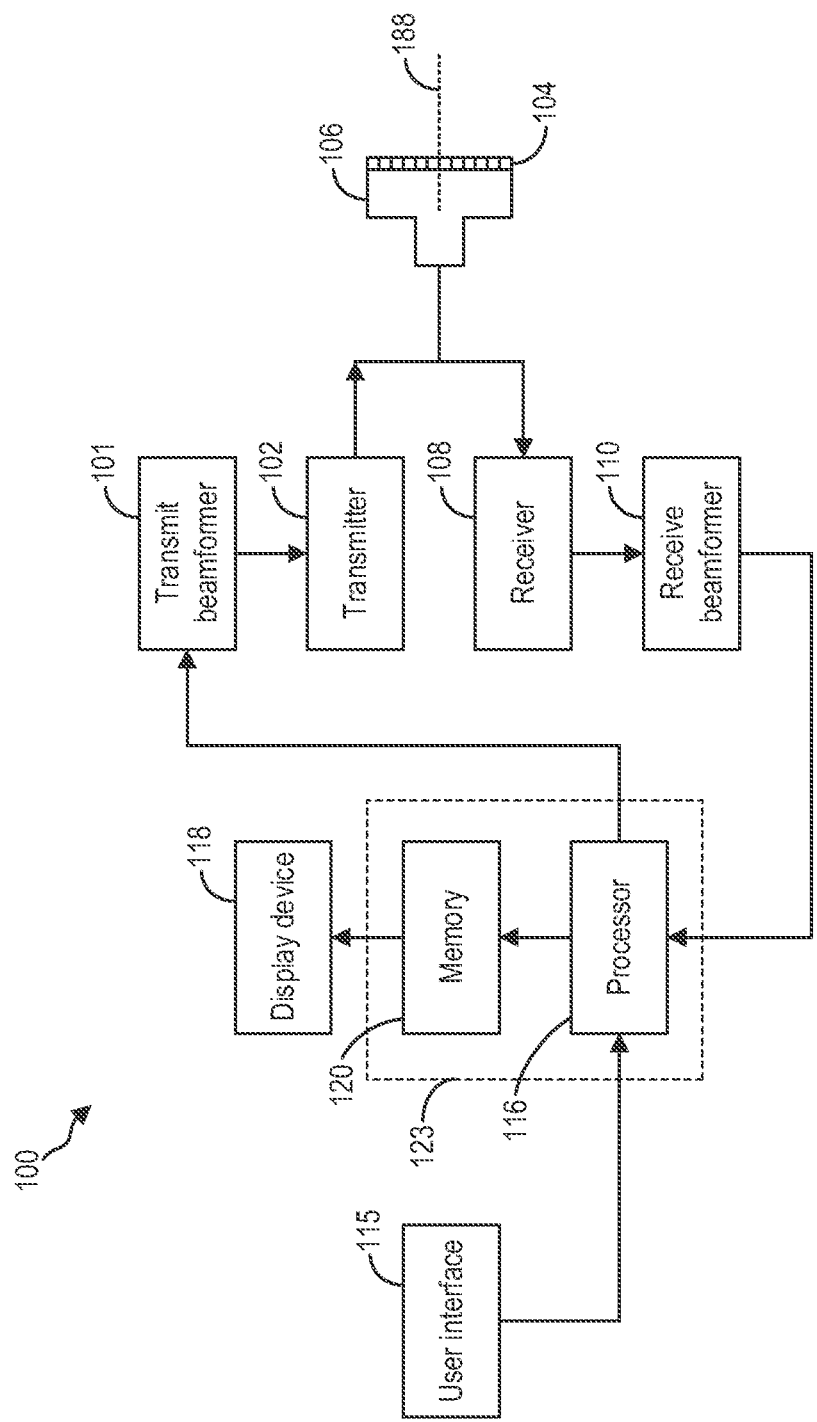
FIG. 4 schematically shows an example portable electronic medical device that may be used with the cable management system of FIGS. 1-3.

Referring now to FIG. 4 a schematic diagram of a portable electronic medical device is shown in accordance with an embodiment. In some embodiments, the portable electronic medical device shown by FIG. 4 is a patient monitor configured to display various patient parameters (e.g., patient information, vitals, etc.). In other embodiments, the portable electronic medical device shown by FIG. 4 may be a different type of medical device, such as an ultrasound imaging system. Though portable electronic medical device 100 is described herein as an ultrasound imaging system by way of example, it should be understood that the present techniques may also be useful when applied to other types of portable electronic medical devices (e.g., patient monitors, portable touchscreen computers, medical monitoring devices such as electrocardiogram monitors, etc.). The present discussion of portable electronic medical device 100 is provided merely as an example of one suitable portable electronic medical device.

The portable electronic medical device 100 includes an accessory 106 electronically coupled to the portable electronic medical device 100. In the embodiment shown by FIG. 4, the accessory 106 is an ultrasound probe including a transmit beamformer 101 and a transmitter 102 that drive elements 104 of a transducer array to emit pulsed ultrasonic signals into a body (not shown). The pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. However, in other embodiments, the accessory 106 may be a different type of accessory (e.g., user input device such as a mouse or keyboard, a printer, electrocardiogram sensor, etc.).

A user interface 115 may be used to control operation of the portable electronic medical device 100, including, to control the input of patient data, to change a scanning or display parameter, to select various modes, operations, and parameters, and the like. In some embodiments, the user interface 115 may include one or more of a rotary, a mouse, a keyboard, a trackball, hard keys linked to specific actions, and/or soft keys that may be configured to control different functions (e.g., during conditions in which the portable electronic medical device 100 is coupled to such devices).

In other embodiments, display device 118 comprises a touch-sensitive display device or touch screen, and the user interface 115 may include a graphical user interface displayed on the display device 118 (e.g., such that an operator of the portable electronic medical device 100 may touch the display device 118 in order to interact with the user interface 115). The touch screen may be a single-touch touch screen that is configured to detect a single contact point at a time or the touch screen may be a multi-touch touch screen that is configured to detect multiple points of contact at a time. For embodiments where the touch screen is a multi-point touch screen, the touch screen may be configured to detect multi-touch gestures involving contact from two or more of a user's fingers at a time. The touch screen may be a resistive touch screen, a capacitive touch screen, or any other type of touch screen that is configured to receive inputs from a stylus or one or more of a user's fingers. According to other embodiments, the touch screen may comprise an optical touch screen that uses technology such as infrared light or other frequencies of light to detect one or more points of contact initiated by a user.

In some embodiments, the user interface 115 may include a proximity sensor configured to detect objects or gestures that are within several centimeters of the proximity sensor. The proximity sensor may be located on either the display device 118 or as part of a touch screen.

For embodiments that include physical controls of the user interface 115, such as buttons, sliders, rotary knobs, keyboards, mice, trackballs, and so on, the physical controls may be provided either alone or in combination with graphical user interface icons displayed on the display device 118. The display device 118 may be configured to display the graphical user interface (GUI) from instructions stored in memory 120. The GUI may include user interface icons to represent commands and instructions. The user interface icons of the GUI are configured so that a user may select commands associated with each specific user interface icon in order to initiate various functions controlled by the GUI. For example, various user interface icons may be used to represent windows, menus, buttons, cursors, scroll bars, and so on.

The portable electronic medical device 100 also includes an electronic controller 123 having a processor 116 configured to control the accessories electronically coupled to the portable electronic medical device 100, such as accessory 106. For example, processor 116 of electronic controller 123 may control transmit beamformer 101, transmitter 102, the receiver 108, and receive beamformer 110. The processor 116 is configured to receive inputs from the user interface 115.

The processer 116 is shown in electronic communication with the accessory 106 (e.g., electrically coupled to accessory 106 via one or more wires, such as conductive wires housed within a cable). The processor 116 may control the accessory 106. For example, the processor 116 may control which of the elements 104 are active and the shape of a beam emitted from the accessory 106 (e.g., in embodiments in which the accessory 106 is an ultrasound probe). The processor 116 is also in electronic communication with a display device 118. The processor 116 may process data received by the accessory 106 for display on the display device 118. For example, in embodiments in which the accessory 106 is a user input device such as a mouse, the processor 116 may update information displayed by the display device (e.g., a position of a cursor) based on user input to the accessory 106. The processor 116 may include a CPU according to an embodiment. According to other embodiments, the processor 116 may include other electronic components capable of carrying out processing functions, such as a GPU, a microprocessor, a DSP, a field-programmable gate array (FPGA), or any other type of processor capable of performing logical operations.

The memory 120 is included for storing acquired data. In embodiments in which the portable electronic medical device 100 is an ultrasound imaging system, the memory 120 may be of sufficient capacity to store at least several seconds' worth of volumes of ultrasound data. The volumes of data are stored in a manner to facilitate retrieval thereof according to its order or time of acquisition. The memory 120 may comprise any known data storage medium. In embodiments in which the portable electronic medical device 100 is a different type of system (e.g., a patient monitor), the memory 120 may store patient parameters and/or patient information.

Figure 5:
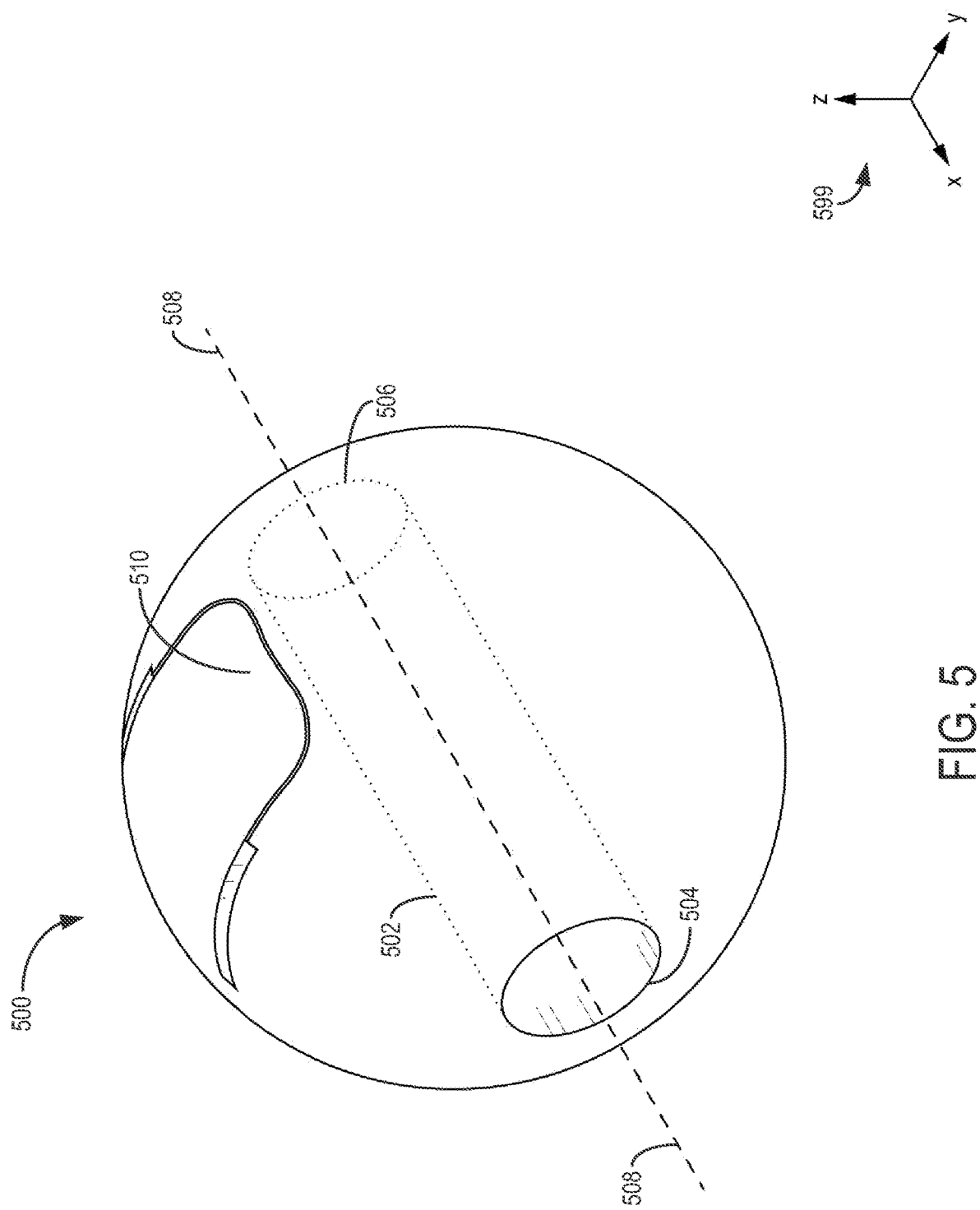
FIG. 5 shows a perspective view of a cable coupler for a cable management system.
Figure 6:
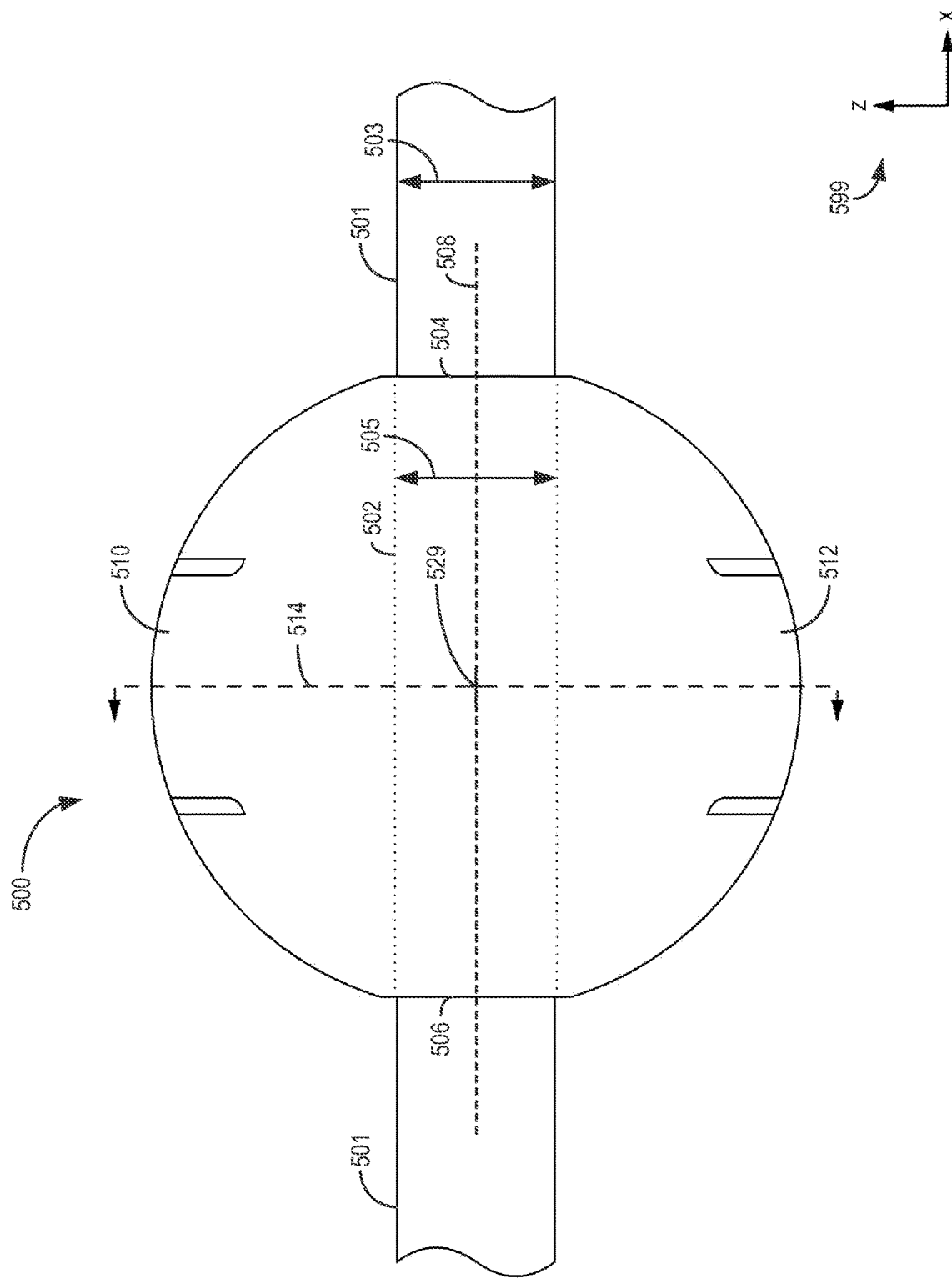
FIG. 6 shows a first side view of the cable coupler of FIG. 5.
Figure 7:
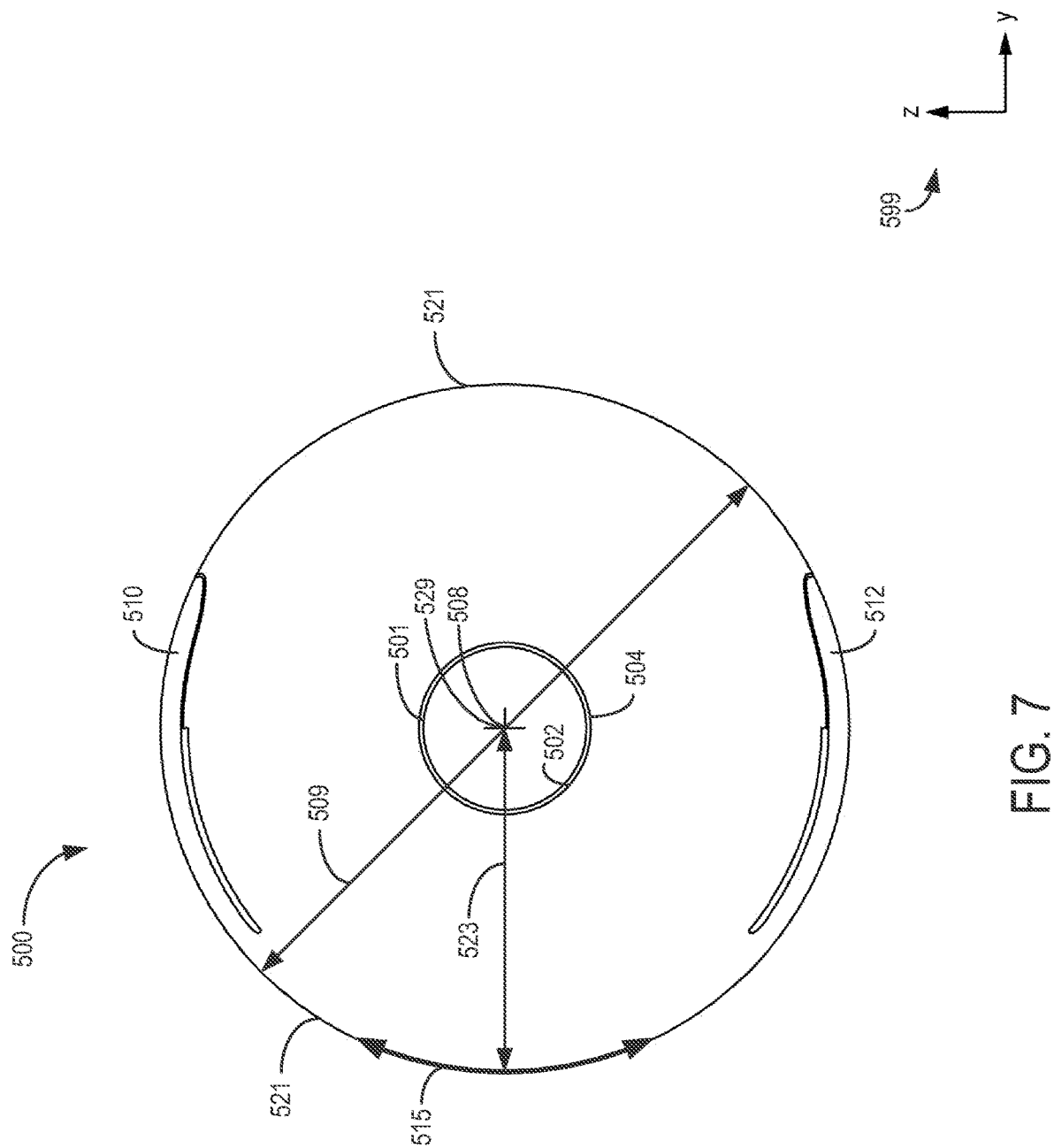
FIG. 7 shows a second side view of the cable coupler of FIGS. 5-6.
Figure 8:
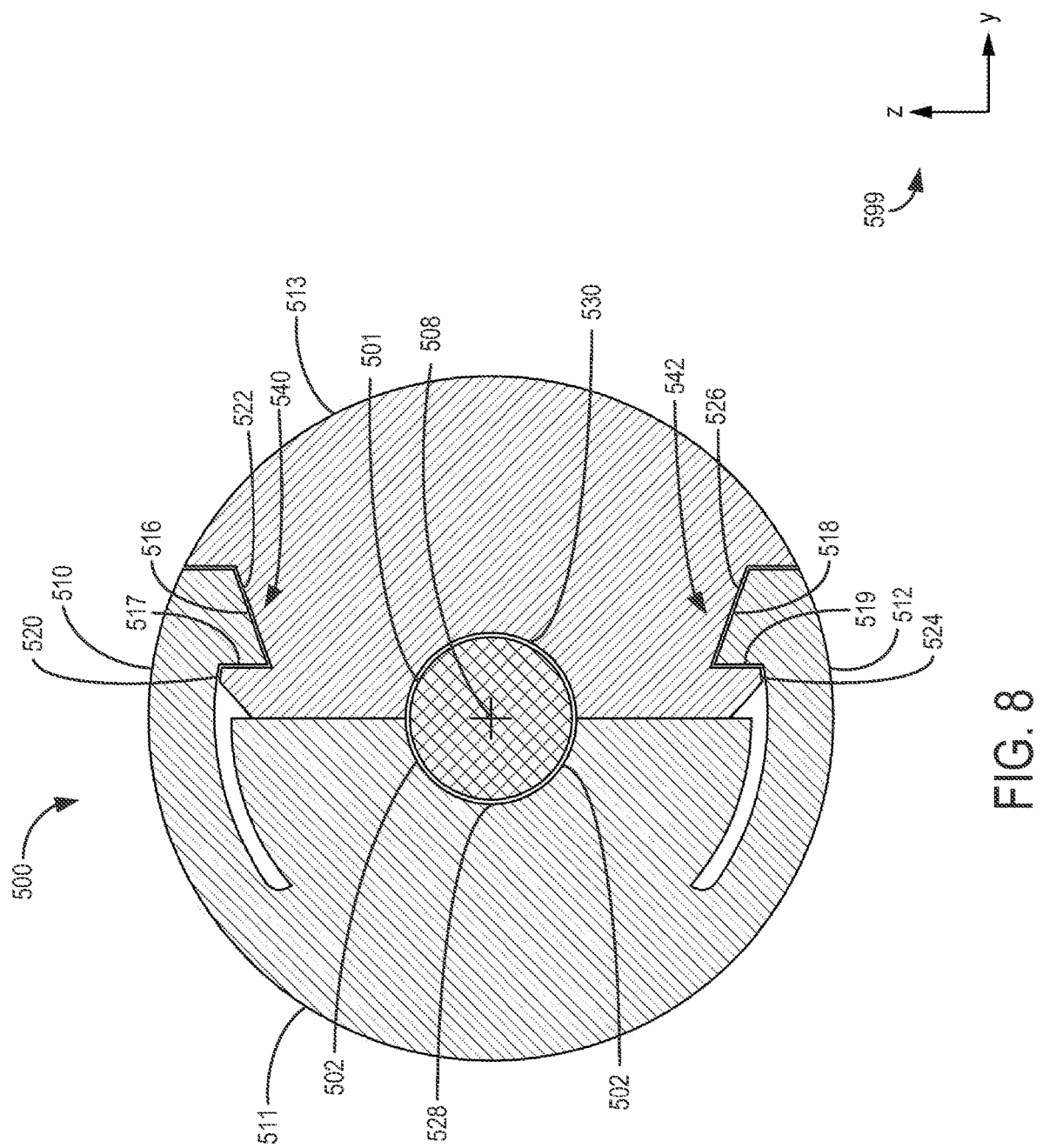
FIG. 8 shows a sectional view of the cable coupler of FIGS. 5-7 in an assembled configuration.
Figure 9:
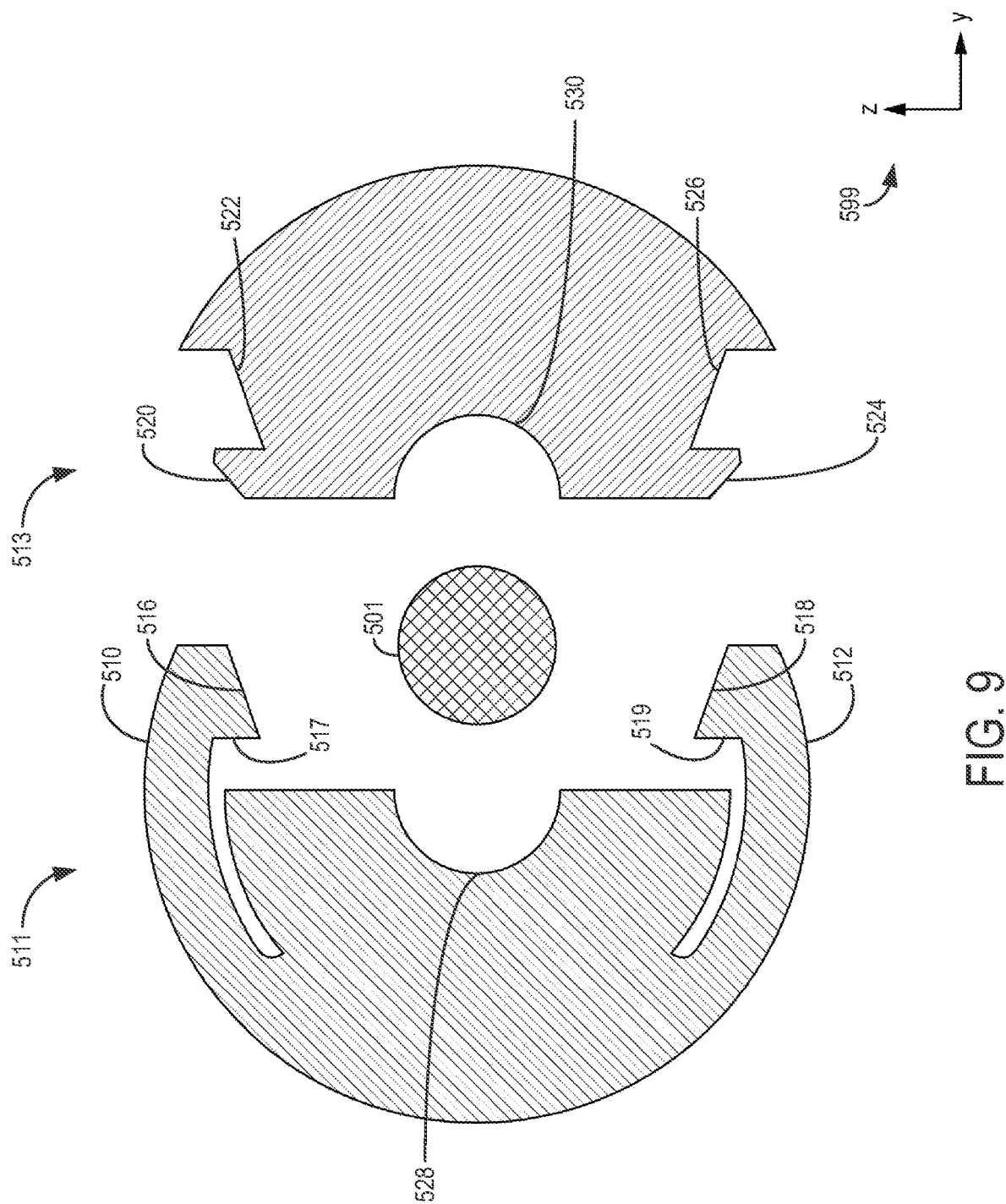
FIG. 9 shows a sectional view of the cable coupler of FIGS. 5-8 in an unassembled configuration.

Referring now to FIGS. 5-9, each of the figures shows a different view of the same cable coupler 500. Reference axes 599 are included for comparison of the views shown. In particular, FIG. 5 shows a perspective view of cable coupler 500, FIG. 6 shows a side view of the cable coupler 500 coupled to a cable 501, FIG. 7 shows another side view of the cable coupler 500 coupled to cable 501, FIG. 8 shows a cross-sectional view of the cable coupler 500 coupled to cable 501, and FIG. 9 shows a cross-sectional view of the cable coupler 500 decoupled from the cable 501. The cable coupler 500 may be included with a cable management system, such as the cable management system 296 described above. In at least one embodiment, the cable coupler 500 may be the same as the cable coupler 290 shown by FIGS. 1 and 3 and described above. Further, cable 501 may be similar to, or the same as, cable 240, cable 242, and/or cable 244.

Cable coupler 500 includes passage 502 shaped to enclose a portion of a cable (e.g., cable 501). The passage 502 includes a first opening 504 and an opposing, second opening 506, with a midpoint of each opening intersected by central axis 508 of passage 502. In some embodiments, the cable coupler 500 may include two separate sections coupled together to form the passage 502, as described further below. One or more of the sections may include interlocking elements, such as first lock element 510 shown by FIG. 5 and opposing, second lock element 512 shown by FIG. 6, described further below.

FIG. 6 shows the side view of the cable coupler 500 with the cable coupler 500 coupled to cable 501. FIG. 6 shows a portion of the cable 501 and not a full length of the cable 501 for illustrative purposes. A diameter 505 of the passage 502 adapted to receive the cable 501 may be slightly larger than a diameter 503 of the cable 501. As one non-limiting example, the diameter 503 of the cable 501 may be 8 millimeters, and the diameter 505 of the passage 502 may be 9 millimeters. As another non-limiting example, the diameter 503 of the cable 501 may be 4 millimeters, and the diameter 505 of the passage 502 may be 5 millimeters. In this configuration, the position of the cable coupler 500 relative to the cable 501 may be maintained by friction between surfaces of the passage 502 and outer surfaces of the cable 501. However, because the diameter 505 of the passage 502 may be slightly larger than the diameter 503 of the cable 501, the position of the cable coupler 500 along the cable 501 may be adjusted by a user (e.g., user of the cable management system including the cable coupler 500, such as the operator of the portable electronic medical device 202 described above) by applying sufficient force to the cable coupler 500 to overcome the friction between the surfaces of the passage 502 and outer surfaces of the cable 501.

FIG. 7 shows another side view of the cable coupler 500. The cable coupler 500 has a diameter 509 and is shaped to fit within a channel of a frame of a cable management system (e.g., channel 218 of frame 204 of cable management system 296, described above). For example, similar to the example described above with reference to FIG. 3, the diameter 509 may be slightly larger than a clearance between opposing walls of the channel adapted to receive the cable coupler 500. As the cable coupler 500 is pressed between the walls, the clearance may temporarily expand as the cable coupler 500 is seated within the channel. In some embodiments, such as the embodiments shown by FIGS. 5-9 and FIG. 10, the cable coupler may have a spherical shape (e.g., a circular cross-section along multiple planes formed by the reference axes 599), and the surfaces of the channel (e.g., inner surfaces and walls) may form a counterpart shape, such that the cable coupler 500 seats against the surfaces. In particular, as shown by FIG. 7, outer surfaces 521 of the cable coupler 500 have a same radius of curvature 523, resulting in a curvature 515 around the central axis 508 of the passage 502. In this configuration, the center of curvature 529 of the outer surfaces 521 is positioned along the central axis 508 (e.g., intercepted by the central axis 508) and the passage 502 extends through the center of curvature 529. However, other embodiments having different shapes are contemplated, such as the embodiments shown by FIGS. 11-12. In such embodiments, at least a portion of the cable coupler is adapted to seat within the respective channel of the frame of the cable management system. Further, in some embodiments, the cable coupler 290 may have a different shape, such as a triangular shape, rectangular shape, hexagonal shape, etc. In such embodiments, the channel includes counterpart surfaces (e.g., surfaces forming a counterpart triangular shape, counterpart rectangular shape, counterpart hexagonal shape, etc.) shaped to engage in face-sharing contact with outer surfaces of the cable coupler in order to maintain the cable coupler seated within the channel.

FIG. 8 shows a cross-sectional view of the cable coupler 500 taken along line 514 shown by FIG. 6. Cable coupler 500 comprises two sections adapted to interlock with each other to enclose a portion of the cable 501. In particular, cable coupler 500 includes first section 511 having first lock element 510 and second lock element 512, and second section 513 having counterpart lock element 540 and counterpart lock element 542. The first lock element 510 of the first section 511 is adapted to couple in interlocking engagement with the counterpart lock element 540 of the second section 513, and the second lock element 512 of the first section 511 is adapted to couple in interlocking engagement with the counterpart lock element 542 of the second section 513. In the view shown by FIG. 8, the first section 511 and second section 513 of the cable coupler 500 are coupled together such that the cable coupler 500 is in an assembled configuration (whereas FIG. 9 shows the cable coupler 500 in an unassembled configuration, with the first section 511 and second section 513 decoupled from each other). In this configuration, an arm 516 of the first lock element 510 is seated within a detent 522 of the counterpart lock element 540, and an arm 518 of the second lock element 512 is seated within a detent 526 of the counterpart lock element 542. A protrusion 520 of the counterpart lock element 540 adjacent to the detent 522 engages with a protruding surface 517 of the arm 516 in order to lock the first lock element 510 to the counterpart lock element 540. Similarly, a protrusion 524 of the counterpart lock element 542 adjacent to the detent 526 engages with a protruding surface 519 of the arm 518 in order to lock the second lock element 512 to the counterpart lock element 542. By locking the first lock element 510 to the counterpart lock element 540 and by locking the second lock element 512 to the counterpart lock element 542 as described above, the first section 511 and the second section 513 of the cable coupler 500 are joined together in interlocking engagement with each other in the assembled configuration around cable 501. In the assembled configuration, inner curved surface 528 of first section 511 and inner curved surface 530 of second section 513 are positioned at opposing sides of the cable 501 in order to form the passage 502 in which the cable 501 sits.

In some embodiments, the first lock element 510 and/or second lock element 512 may include more than one arm, with each arm configured to engage with a respective detent of the respective counterpart lock element (e.g., counterpart lock element 540 and/or counterpart lock element 542). In some embodiments, a position of each arm within each respective detent may be adjustable, such that the user may increase or decrease a length between the inner curved surface 528 of first section 511 and inner curved surface 530 of second section 513 by adjusting the positions of the arms within the detents. In this configuration, the diameter of the passage 502 may be increased by the user in order to accommodate cables of various sizes (e.g., thickness).

Figure 10:
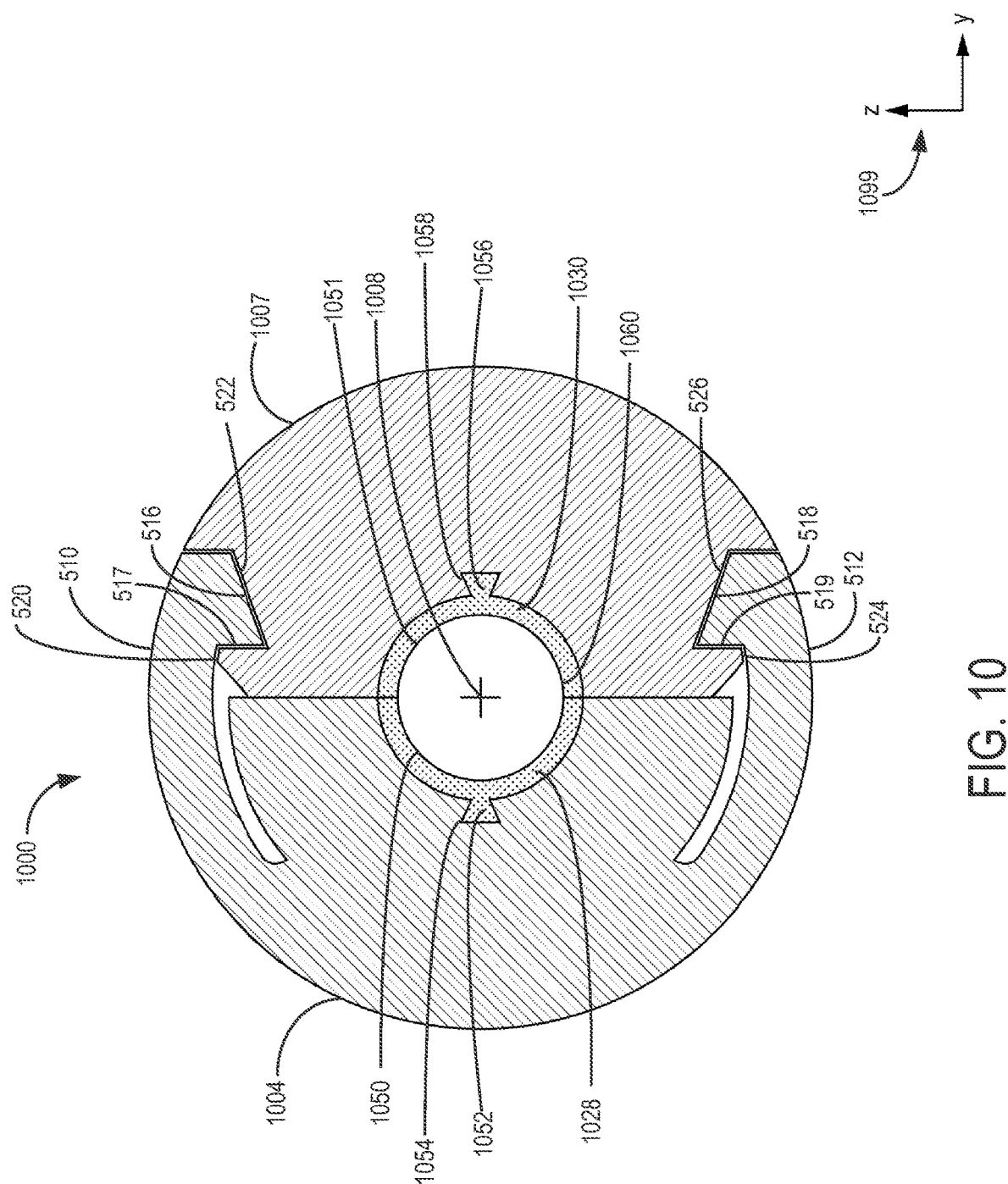
FIG. 10 shows a sectional view of another cable coupler for a cable management system.

Referring now to FIG. 10, a cross-sectional view of a cable coupler 1000 is shown according to another embodiment. The cross-sectional view of cable coupler 1000 may be taken along a line similar to line 514 shown by FIG. 6.

Further, reference axes 1099 may be in a similar arrangement relative to reference axes 599 shown by FIGS. 5-9. In particular, the z-axis of reference axes 1099 may be parallel with the z-axis of reference axes 599, the y-axis of reference axes 1099 may be parallel with the y-axis of reference axes 599, and the x-axis of reference axes 1099 may be parallel with the x-axis of reference axes 599. Cable coupler 1000 may be included with a cable management system, such as the cable management system 296 described above. Cable coupler 1000 is configured to seat within a channel of a frame of the cable management system, similar to the examples described above (e.g., similar to cable coupler 290 adapted to seat within channel 218 of frame 204, and similar to cable coupler 500). Cable coupler 1000 includes several features similar to those described above with reference to cable coupler 500. Similar features may be labeled similarly and not re-introduced.

Cable coupler 1000 includes a first section 1004 and a second section 1007. In the view shown by FIG. 10, the cable coupler 1000 is in an assembled configuration, with the first section 1004 joined in interlocking engagement with the second section 1007. In this configuration, the first section 1004 and second section 1007 form passage 1060 adapted to enclose a portion of a cable (e.g., cable 501 shown by FIGS. 6-9, cables 240, 242, and/or 242 shown by FIGS. 1-2, etc.). However, in the embodiment shown by FIG. 10, each of the first section 1004 and second section 1007 includes an insert or coating formed of a different material and configured to increase an amount of friction between the surfaces of the passage 1060 and the respective cable seated within the passage 1060 (e.g., during conditions in which the cable coupler 1000 is coupled to the cable). Specifically, first section 1004 includes inner layer 1028 comprising first inner surface 1050, and second section 1007 includes inner layer 1030 comprising second inner surface 1051. The inner layer 1028 and inner layer 1030 may each be formed from a material having a relatively high coefficient of friction (e.g., rubber). The inner layer 1028 and inner layer 1030 may each increase an ability of the cable coupler 1000 to be maintained in position relative to the cable during conditions in which the cable coupler 1000 is coupled to the cable (e.g., conditions in which inner surface 1050 of inner layer 1028 and inner surface 1051 of inner layer 1030 are each in face-sharing contact with outer surfaces of the cable). Further, the first section 1004 includes a tapered groove 1054 shaped to engage with a tab 1052 of the inner layer 1028, and the second section 1007 includes a tapered groove 1058 shaped to engage with a tab 1056 of the inner layer 1030. The engagement of tab 1052 with groove 1054 may decrease a likelihood of decoupling the inner layer 1028 from the first section 1004, and the engagement of tab 1056 with tapered groove 1058 may decrease a likelihood of decoupling the inner layer 1030 from the second section 1007.

Referring now to FIG. 11, a side view of a cable coupler 1100 is shown according to another embodiment. Cable coupler 1100 may be seated within a channel of a frame of a cable management system in order to maintain a position of a cable relative to the frame, similar to the examples above. For example, cable coupler 1100 may be included by cable management system 296 shown by FIGS. 1-2 and may seat within channel 218 or channel 212 in order to maintain a position of cables 240, 242, or 244 relative to frame 204. Reference axes 1199 are included for comparison of the view shown with the views described above. For example, the z-axis of reference axes 1199 may be parallel with the z-axis of reference axes 599 and the z-axis of reference axes 1099, and the y-axis of reference axes 1199 may be parallel with the y-axis of reference axes 599 and the y-axis of reference axes 1099.

The cable coupler 1100 includes a head portion 1102 having a diameter 1106. The diameter 1106 may be sized such that the head portion 1102 seats within the channel of the frame and is maintained in position by walls of the channel, similar to the examples described above (e.g., similar to walls 220 and 222 of channel 218 of frame 204). In at least one example, the diameter 1106 of the head portion 1102 may be the same as the diameter 509 of cable coupler 500 of FIGS. 5-9 and/or diameter 253 of cable coupler 290 of FIGS. 1 and 3. In this configuration, the head portion 1102 engages with the surfaces of the channel of the frame in order to couple with the channel. In the configuration shown by FIG. 11, the head portion 1102 has a spherical shape (e.g., similar to the spherical shape of the cable coupler 290 and/or cable coupler 500 described above). In other embodiments, the head portion 1102 may have a different shape (e.g., similar to the examples described above, where the shape may be triangular, rectangular, hexagonal, etc.).

The cable coupler 1100 additionally includes a tapered portion 1114 having a thickness 1121 and extending outward from the head portion 1102. The thickness 1121 of the tapered portion 1114 is less than the diameter 1106 (which may be referred to herein as a thickness) of the head portion 1102. The tapered portion 1114 and head portion 1102 may be formed together (e.g., molded together) as a single unit. The tapered portion includes a first arm 1108 and an opposing, second arm 1110. An end 1109 of the first arm 1108 is separated from an end 1111 of the second arm 1110 by a first clearance 1116. Each of the first arm 1108 and second arm 1110 curve away from each other with a same radius of curvature, such that a second clearance 1112 is formed between an inner surface 1113 of the first arm 1108 and an inner surface 1115 of the second arm 1110. The second clearance 1112 may be referred to herein as a passage between the first arm 1108 and second arm 1110 (e.g., passage 1112). The second clearance 1112 is larger than the first clearance 1116. The second clearance 1112 is sized such that a cable (e.g., cables 240, 242, or 244 shown by FIGS. 1-2, cable 501 shown by FIGS. 6-9, etc.) may seat between the first arm 1108 and second arm 1110 within the second clearance 1112.

In order to seat the cable between the first arm 1108 and second arm 1110, the cable may be pressed through the first clearance 1116 and into the second clearance 1112 in insertion direction 1117. As the cable is pressed into the first clearance 1116, the first arm 1108 and second arm 1110 may move outward from each other (e.g., bend outward), increasing the length of first clearance 1116 such that the cable may fit through the first clearance 1116 and seat between the first arm 1108 and second arm 1110 in the second clearance 1112. After the cable is seated in the second clearance 1112, a rigidity of the first arm 1108 and second arm 1110 causes the first arm 1108 and second arm 1110 to contract toward each other, reducing the length of the first clearance 1116 to less than the diameter of the cable and locking the cable between the first arm 1108 and second arm 1110 in the second clearance 1112. In this configuration, the position of the cable may be maintained by the cable coupler 1100 while the cable coupler 1100 is seated within the channel of the frame of the cable management system without positioning the cable within the channel, which may enable a user of the cable management system to more easily adjust a position of the cable relative to the frame. Further, in this configuration, the cable coupler 1100 may be formed (e.g., molded) as a single unit without additional components or pieces, which may reduce an assembly time and/or cost of the cable management system.

Referring now to FIG. 12, a cable coupler 1200 for a cable management system is shown according to another embodiment. Cable coupler 1200 may be seated within a channel of a frame of a cable management system in order to maintain a position of a cable relative to the frame, similar to the examples above. For example, cable coupler 1200 may be included by cable management system 296 shown by FIGS. 1-2 and may seat within channel 218 or channel 212 in order to maintain a position of cables 240, 242, or 244 relative to frame 204. Reference axes 1299 are included for comparison of the view shown with the views described above. For example, the z-axis of reference axes 1299 may be parallel with the z-axis of reference axes 599 and the z-axis of reference axes 1099, and the y-axis of reference axes 1299 may be parallel with the y-axis of reference axes 599 and the y-axis of reference axes 1099.

Cable coupler 1200 includes a rounded end 1202 having a width 1206 sized to fit within the channel of the frame of the cable management system. As one example, the width 1206 may be the same as the diameter 253 of cable coupler 290 shown by FIGS. 1 and 3, and/or the diameter 509 of cable coupler 500 shown by FIGS. 5-9. Cable coupler 1200 includes passage 1216 extending along central axis 1218 and having diameter 1219. The diameter 1219 of the passage 1216 is sized such that a cable (e.g., cable 240, 242, or 242 shown by FIGS. 1-2, cable 501 shown by FIGS. 6-9, etc.) may seat within the passage 1216 in order to be maintained in position relative to the frame by the cable coupler 1200. For example, similar to the embodiment shown by FIGS. 5-9 and described above, the cable coupler 1200 may be assembled by coupling together a first section and a second section around the cable, with the first section including a first lock element 1204 and a second lock element 1214, and with the second section including respective counterpart lock elements adapted to couple in interlocking engagement with the lock elements of the first section.

The cable coupler 1200 further includes a tapered section 1208 having an end 1210 with a reduced size relative to the rounded end 1202. In particular, a width 121 of the end 1210 is less than the width 1206 of the rounded end 1202. During conditions in which a cable is seated within the passage 1216 and the rounded end 1202 is seated within the channel of the frame of the cable management system, a user of the cable management system may adjust the position of the cable coupler 1200 and the respective coupled cable by grasping the end 1210 and moving the cable coupler 1200 within the channel. The reduced size of the end 1210 may increase an ease with which the user may move the cable coupler 1200 (e.g., slide and/or rotate the cable coupler 1200 within the channel).

Referring now to FIG. 13, a flow chart illustrating a method 1300 for cable management via a cable management system is shown. The cable management system may be the cable management system 296 shown by FIGS. 1-3 and described above. Further, cable couplers included by the cable management system may include the cable coupler 500 shown by FIGS. 5-9 and described above, cable coupler 1000 shown by FIG. 10 and described above, cable coupler 1100 shown by FIG. 11 and described above, and/or cable coupler 1200 shown by FIG. 12 and described above.

At 1302, a portable electronic medical device is seated within the frame of the cable management system. The portable electronic medical device may be the portable electronic medical device 202 shown by FIGS. 1-2 and described above, or portable electronic medical device 100 shown schematically by FIG. 4 and described above. Further, as described above, although the portable electronic medical device may be described herein as an ultrasound imaging system by way of example, it should be understood that the present techniques may also be useful when applied to other types of portable electronic medical devices (e.g., portable touchscreen computers, medical monitoring devices such as electrocardiogram monitors, etc.), The present discussion of the portable electronic medical device is provided merely as an example of one suitable portable electronic medical device including cables that may be managed via the cable management system.

Seating the portable electronic medical device within the frame of the cable management system may include pressing a housing of the portable electronic medical device (e.g., housing 206 shown by FIGS. 1-2 and described above) through a main opening of the frame (e.g., main opening 210 shown by FIGS. 1-3 and described above) and positioning outer surfaces of the housing in face-sharing contact with inner surfaces of the frame. In this configuration, one or more cable ports of the portable electronic medical device may be accessible by a user of the cable management system (e.g., a clinician) via a side opening of the frame (e.g., side opening 224 of frame 204 shown by FIGS. 1-2 and described above).

At 1304, an electronic accessory is coupled to a port of the portable electronic medical device through an opening of the frame. The electronic accessory may be the accessory 106 described above with reference to FIG. 4 (e.g., a user input device, ultrasound probe, printer, patient monitoring sensor, etc.), and the opening of the frame may be the side opening described above (e.g., similar to the side opening 224 shown by FIGS. 1-2 and described above). Coupling the electronic accessory to the portable electronic medical device may electronically couple the electronic accessory to an electronic controller of the portable electronic medical device (e.g., electronic controller 123 shown by FIG. 4). Coupling the electronic accessory to the port of the portable electronic medical device may include coupling a connector of a cable of the electronic accessory to the respective port of the portable electronic medical device. The connector may be similar to (or the same as) first connector 234, second connector 236, or third connector 238 shown by FIGS. 1-2 and described above. The port may be similar to (or the same as) first port 228, second port 230, or third port 232 shown by FIGS. 1-2 and described above.

At 1306, the cable of the electronic accessory is seated within a passage of a cable coupler of the cable management system. The cable may be similar to (or the same as) the first cable 240, second cable 242, and/or third cable 244 described above with reference to FIGS. 1-2, and/or cable 501 shown by FIGS. 6-9 and described above. The cable coupler may be similar to (or the same as) the cable coupler 290 shown by FIGS. 1 and 3, the cable coupler 500 shown by FIGS. 5-9, the cable coupler 1000 shown by FIG. 10, the cable coupler 1100 shown by FIG. 11, or the cable coupler 1200 shown by FIG. 12. The passage may be similar to (or the same as) passage 292 shown by FIGS. 1 and 3, passage 502 shown by FIGS. 5-8, passage 1060 shown by FIG. 10, passage 1112 shown by FIG. 11, or passage 1216 shown by FIG. 12.

Seating the cable of the electronic accessory within the passage of the cable coupler of the cable management system at 1306 may optionally include, at 1308, positioning a first section of the cable coupler against the cable of the electronic accessory and enclosing the cable coupler around the cable by locking a second section of the cable coupler to the first section. For example, as described above with reference to the embodiment shown by FIGS. 5-9, the cable coupler may include two separate sections coupled together to form the passage (e.g., similar to, or the same as, first section 511 and second section 513 shown by FIGS. 8-9, first section 1004 and second section 1007 shown by FIG. 10, or first and second sections of the cable coupler 1200 shown by FIG. 12). One or more of the sections may include lock elements, such as first lock element 510 shown by FIG. 5 and opposing, second lock element 512 shown by FIG. 6. The lock elements may couple in interlocking engagement with each other in order to lock the first section and second section together around the cable, with the cable disposed in the passage.

In other embodiments, seating the cable of the electronic accessory within the passage of the cable coupler of the cable management system at 1306 may optionally include, at 1310, pressing the cable into a clearance formed between opposing arms of the cable coupler. The clearance may be similar to (or the same as) the clearance 1112 (e.g., passage 1112) shown by FIG. 11 and described above. Pressing the cable into the clearance may temporarily move the opposing arms of the cable coupler away from each other, similar to the example described above with reference to FIG. 11. After the cable is seated in the clearance, the opposing arms contract toward each other, reducing the length of the clearance and locking the cable between the opposing arms.

At 1312, the cable coupler is seated within a channel of the frame. The channel of the frame may be similar to (or the same as) the channel 218 or the channel 212 shown by FIGS. 1-3 and described above. Seating the cable coupler within the channel may include pressing the cable coupler between opposing walls of the channel (e.g., first wall 214 and second wall 216, or third wall 220 and fourth wall 222) in order to momentarily expand a length between the walls by bending and/or flexing the walls outward relative to each other. The cable coupler may then fit between the walls to seat against an inner surface of the channel. After seating in face-sharing contact with the inner surface, the opposing walls contract toward each other to maintain the cable coupler in the seated position within the channel. The cable coupler may have a spherical shape or include a spherical portion sized to fit within the channel (e.g., similar to, or the same as, the embodiments shown by FIGS. 5-11). However, in some embodiments, the cable coupler may include a rounded and non-spherical portion shaped to fit within the channel (e.g., similar to, or the same as, the embodiment shown by FIG. 12).

The technical effect of seating a cable of an electronic accessory within a passage of a cable coupler of a cable management system and seating the cable coupler within a channel of a frame of the cable management system is to maintain a position of the cable relative to the frame.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

We claim:

1. A system, comprising:
   a frame for a portable electronic medical device, the frame including a first wall and an opposing, second wall forming inner surfaces of a channel; and
   a cable coupler adapted to seat within the channel, including:
      counterpart outer surfaces shaped to engage the inner surfaces; and
      a passage shaped to enclose a portion of a cable,
   wherein the channel is sized and shaped to simultaneously hold multiple cable couplers.

2. The system of claim 1, wherein, in a first configuration where the cable coupler is not seated within the channel, the first wall and second wall are separated by a first clearance, and in a second configuration where the cable coupler is seated within the channel, the first wall and second wall are deformed by the cable coupler and separated by a second clearance.

3. The system of claim 1, wherein the channel is a first channel, and the frame further includes a third wall and an opposing, fourth wall forming a second channel, with the cable coupler adapted to seat in either of the first or second channels.

4. The system of claim 1,
   wherein the cable coupler has a spherical shape and the outer surfaces and inner surfaces have a same radius of curvature, and wherein a clearance between a terminating end of the first wall and a terminating end of the second wall is smaller than a diameter of the cable coupler.

5. The system of claim 4, wherein the channel is positioned at a bottom end of the frame, the bottom end perpendicular to the main opening and side opening.

6. The system of claim 1, wherein the frame includes a main opening extending from a front end to a rear end of the frame and a side opening positioned at a side of the frame, the main opening shaped to receive the portable electronic medical device with an electronic communication port of the portable electronic medical device positioned within the side opening.

7. The system of claim 1, wherein the cable coupler is one of a plurality of cable couplers, and wherein at least one cable coupler of the plurality of cable couplers is a different color relative to each other cable coupler of the plurality of cable couplers.

8. A method, comprising:
   seating a portable electronic medical device in a frame of a cable management system;

coupling a first cable and a second cable to the portable electronic medical device through an opening of the frame;

seating the first cable within a passage of a first cable coupler;

seating the second cable within a passage of a second cable coupler, and seating the first cable coupler and the second cable coupler within a channel of the frame such that the first cable coupler and the second cable coupler are simultaneously seated within the channel.

9. The method of claim 8, wherein seating the first cable within the passage of the first cable coupler further comprises:

positioning a first section of the first cable coupler against the first cable; and enclosing the first cable coupler around the first cable by locking a second section of the first cable coupler to the first section.

10. The method of claim 9, wherein locking the second section of the first cable coupler to the first section includes coupling a detent of the second section in interlocking engagement with an arm of the first section.

11. The method of claim 8, wherein seating the first cable within the passage of the first cable coupler further comprises pressing the first cable into the passage between opposing arms of the first cable coupler.

12. The method of claim 11, wherein pressing the first cable into the passage between the opposing arms includes:

first, expanding the opposing arms outward from each other via the first cable; and then, contracting the opposing arms around the first cable.

* * * * *